(12) United States Patent
Robertson et al.

(10) Patent No.: US 12,428,370 B2
(45) Date of Patent: Sep. 30, 2025

(54) HALOALLYLAMINE DUAL AMINE OXIDASE INHIBITORS

(71) Applicant: Syntara Limited, Frenchs Forest (AU)

(72) Inventors: Alan Duncan Robertson, Warawee (AU); Alison Dorothy Findlay, Frenchs Forest (AU); Alberto Buson, Macquarie Park (AU); Craig Ivan Turner, Frenchs Forest (AU); Dieter Wolfgang Hamprecht, Frenchs Forest (AU); Jonathan Stuart Foot, Frenchs Forest (AU); Mandar Deodhar, Frenchs Forest (AU); Wolfgang Jarolimek, Frenchs Forest (AU); Serena Becchi, Wollstonecraft (AU); Bernard Walter Balleine, Paddington (AU); Marcella Canton, Padua (IT); Libero Vitiello, Padua (IT); Bert Blaauw, Padua (IT)

(73) Assignee: Syntara Limited, Frenchs Forest (AU)

( * ) Notice: Subject to any disclaimer, the term of this patent is extended or adjusted under 35 U.S.C. 154(b) by 427 days.

(21) Appl. No.: 18/012,540

(22) PCT Filed: Jun. 25, 2021

(86) PCT No.: PCT/AU2021/050675
§ 371 (c)(1),
(2) Date: Dec. 22, 2022

(87) PCT Pub. No.: WO2021/258159
PCT Pub. Date: Dec. 30, 2021

(65) Prior Publication Data
US 2023/0257342 A1   Aug. 17, 2023

(30) Foreign Application Priority Data

Jun. 26, 2020   (AU) ................. 2020902152

(51) Int. Cl.
*C07C 255/54*   (2006.01)
*A61P 9/00*   (2006.01)
*A61P 21/00*   (2006.01)

(52) U.S. Cl.
CPC .............. *C07C 255/54* (2013.01); *A61P 9/00* (2018.01); *A61P 21/00* (2018.01)

(58) Field of Classification Search
CPC .................................................. C07C 255/54
See application file for complete search history.

(56) References Cited

U.S. PATENT DOCUMENTS

2011/0269811 A1   11/2011   Wang et al.

FOREIGN PATENT DOCUMENTS

| AU | 2018287777 B2 | 5/2020 |
| CN | 109251166 A | 1/2019 |
| WO | 2013163675 A1 | 11/2013 |
| WO | 2019024924 A1 | 2/2019 |

*Primary Examiner* — Golam M Shameem
(74) *Attorney, Agent, or Firm* — Haley Guiliano LLP

(57) ABSTRACT

The present invention relates to novel compounds which are capable of inhibiting semicarbazide-sensitive amine oxidase (SSAO/VAP-1) and monoamine oxidase B (MAO-B). These compounds are useful for treatment of a variety of neuromuscular diseases, such as muscular dystrophies, and neuroinflammatory diseases, including both peripheral and central disorders in human subjects, as well as in pets and livestock. In addition, the present invention relates to pharmaceutical compositions containing these compounds, as well as various uses thereof.

11 Claims, 9 Drawing Sheets

PXS-5131 orally administered to Sprague Dawley @ 0.6 mg/kg MAO-B activity in brain

HALOALLYLAMINE DUAL AMINE OXIDASE INHIBITORS

CROSS-REFERENCE TO RELATED APPLICATIONS

This application is a United States National Phase Application filed under 35 U.S.C. § 371 from International Patent Application No. PCT/AU2021/050675, filed on Jun. 25, 2021, which claims the benefit of priority from Australian Patent Application No. 2020902152, filed on Jun. 26, 2020, the contents, and disclosures of each of these applications are incorporated herein by reference in their entireties.

TECHNICAL FIELD

The present invention relates to novel compounds which are capable of inhibiting semicarbazide-sensitive amine oxidase (SSAO/VAP-1) and monoamine oxidase B (MAO-B). These compounds are useful for treatment of a variety of neuromuscular diseases, such as muscular dystrophies, and neuroinflammatory diseases, including both peripheral and central disorders in human subjects, as well as in pets and livestock. In addition, the present invention relates to pharmaceutical compositions containing these compounds, as well as various uses thereof.

BACKGROUND

In most organisms, including humans, two families of mammalian amine oxidases metabolize various mono-, di-, and polyamines produced endogenously or absorbed from exogenous sources. The first family includes the monoamine oxidases (MAO-A and MAO-B) which are present in the mitochondria of most cell types and use covalently bound flavin adenine dinucleotide (FAD) as the cofactor. Polyamine oxidase is another FAD-dependent amine oxidase which oxidatively deaminates spermine and spermidine. The second family is dependent on copper and uses other co-factors apart from FAD, such as an oxidized tyrosine residue (abbreviated as TPQ or LTQ). One member of this family is semicarbazide-sensitive amine oxidase (SSAO), also known as primary amine oxidase, plasma amine oxidase and benzylamine oxidase, and is identical to vascular adhesion protein-1 (VAP-1—from here on described as SSAO/VAP-1). Diamine oxidase (DAO) and the lysyl oxidase family of proteins (lysyl oxidase (LOX) and lysyl oxidase-like (LOXL) 1-4) also belong to this second family. Pharmacologically, MAO-A is selectively inhibited by clorgyline, MAO-B by L-deprenyl and SSAO/VAP-1 by semicarbazide.

Monoamine oxidase (MAO) activity is responsible for the oxidative deamination of endogenous amines such as serotonin, dopamine, adrenaline, noradrenaline, arylalkylamines and a number of amine xenobiotics. Although MAO-A and MAO-B share a common enzymatic role in the metabolism of amines, they have only a 70% sequence similarity, are encoded by different genes (Bach A. W., et al., *Proc. Natl. Acad. Sci. USA* 1988, 85, 4934-4938) and are distributed differently in the body. MAO-A has a higher affinity for substrates such as tyramine, serotonin, adrenaline and noradrenaline, whereas MAO-B shows a preference for dopamine, phenylethylamine and other trace aryalkylamines. MAO-B is expressed in multiple organs including the brain, heart, adipose tissue, pancreas, lung, kidney, muscle and liver.

Non-selective MAO inhibitors that inhibit both MAO-B and MAO-A have the potential to induce hypertensive crisis when dietary tyramine is ingested and therefore come with certain dietary limitations (Gardner D. M., et. al., *J. Clin. Psychiatry* 1996, 57, 99-104). In addition, non-selective inhibitors increase the potential for monoamine interactions with other medications. Thus, for medicinal applications there is a need for MAO-B inhibitors with a high selectivity over MAO-A.

SSAO/VAP-1 is an ectoenzyme containing a very short cytoplasmic tail, a single transmembrane domain, and a large, highly glycosylated extracellular domain which contains the active site for the amine oxidase activity (Salmi M. & Jalkanen S. *Science* 1992, 257, 1407-1414). SSAO/VAP-1 is also present in a soluble form circulating in the plasma of some animals. It has been shown that this form is a cleaved product of membrane-bound SSAO/VAP-1 (Stolen C. M., et al., *Circ. Res.* 2004, 95, 50-59). SSAO/VAP-1 is highly expressed in adipose tissue, lung, liver, aorta and muscle tissue. SSAO/VAP-1 appears to have two physiological functions: the first is the amine oxidase activity and the second is cell adhesion activity. Both activities are associated with inflammatory processes. Inhibitors of the amine oxidase activity of SSAO/VAP-1 have been found to interfere with leukocyte rolling, adhesion and extravasation and, similar to SSAO/VAP-1 antibodies, exhibit anti-inflammatory properties (Foot J. S., et al., *J. Pharm. Exp. Ther.*, 2013, 347, 365-374).

Oxidative deamination of primary monoamines by both MAO-B and SSAO/VAP-1 produces ammonia ($NH_3$), aldehydes and hydrogen peroxide ($H_2O_2$), agents with established toxicity that can cause significant inflammation through their promiscuous reactivity and oxidative stress. During the SSAO/VAP-1 amine oxidase catalytic cycle the covalently bound cofactor, TPQ, is first reduced, and then re-oxidized by oxygen in the presence of copper with the generation of ammonia and hydrogen peroxide as by-products. Likewise, MAO-B acting through a single-electron transfer process oxidizes amines to aldehydes and ketones with concomitant reduction of flavin adenine dinucleotide (FAD) to the reduced form, $FADH_2$. The cofactor is then re-oxidized by oxygen producing hydrogen peroxide. It has been speculated that excessive hydrogen peroxide concentrations can be deleterious and may contribute to the pathology of various inflammatory and neurodegenerative processes (Götz M. E., et al., *Pharmacol Ther.* 1994, 63, 37-122).

Neuromuscular disease is a term used to describe a variety of disorders where the underlying pathophysiology of the disease affects the muscle function either directly through degradation of the muscle tissue, or indirectly, affecting the nerves and neuromuscular junctions controlling the muscle. Direct effects on muscle can lead to muscle wasting and decreased mobility, whereas the indirect central nervous system (CNS)-mediated neuromuscular effects range from occasional spasticity to paralysis. Diseases linked to muscle wasting are further categorised as muscular dystrophies and include Duchenne muscular dystrophy (DMD), Becker muscular dystrophy, facioscapulohumeral muscular dystrophy and myotonic muscular dystrophy. Indirect neuromuscular diseases are categorized as central disorders and include Parkinson's disease, multiple sclerosis, Huntington's disease and Creutzfeldt-Jakob disease.

Neuroinflammatory disease is a term used to describe a variety of disorders where the immune response leads to the degeneration of the nervous system, leading to chronic inflammation. This inflammation can lead to neurodegenerative diseases, such as Alzheimer's disease, Parkinson's disease, prion disease, motor neurone diseases, Huntington's disease, spinocerebellar ataxia and spinal muscular atrophy. In addition, neuroinflammation is an underlying cause of neurological diseases, such as epilepsy, stroke and brain trauma.

DMD is the most prevalent form of muscular dystrophy. It is a lethal neuromuscular disorder, genetically inherited as an X chromosome-linked disease and caused by mutations in the dystrophin gene. Principally, boys are affected, with an incidence of about one in 3,500 live male births. Muscular degeneration is characteristic of the disease, with debilitating effects on mobility and daily functioning from a young age. Cardiac fibrosis and respiratory failure are the most common cause of mortality in DMD patients. There is no cure for DMD and current treatment options focus on alleviation of symptoms and management of complications, and center around the use of corticosteroids, surgery, ventilation and physiotherapy. Although recent high profile advances in splicing modulators and gene therapy may allow for partial restoration of dystrophin function in a minority of patients, the long-term benefits of such treatments are, as yet, unclear and significant need for alternative or additional treatment options remains.

Parkinson's disease is the most common of the CNS disorders. It results from damage to the nerve cells in a region of the brain that produces dopamine, a chemical that is vital for the control of muscles and movement. It is a progressive, degenerative neurological condition that causes trembling in the hands, arms, legs, jaw, and face; rigidity or stiffness of the limbs or trunk; slowness of body movements; and unstable posture and difficulty in walking. It typically presents later in life, with an onset of symptoms from age 60 onwards, and is thought to affect more than 10 million people worldwide. Treatments can presently only slow progression and address the symptoms. First line treatments include the use of levodopa (a dopamine precursor able to cross the blood-brain barrier) to increase brain dopamine, as well as carbidopa and MAO-B inhibitors to reduce the metabolism of levodopa and dopamine. Anticholinergics and medicinal marijuana are also prescribed to lessen dyskinesia.

MAO-B activity increases oxidative stress in muscle and systemically, leading to compromised mitochondrial function and an increase in reactive oxygen species. Myogenic cell cultures from both mdx mice (an animal bred to exhibit the hallmark characteristics of DMD patients, and established as the relevant model for human disease) and DMD patients are more susceptible to oxidative stress. This sensitivity was abrogated by treatment with an inhibitor (safinamide) of MAO-B in vitro. Pharmacological inhibition of MAO-B has also shown to be efficacious in vivo; when given to 3-month old mdx mice, safinamide reduced myofiber damage and oxidative stress, and improved muscle function (Vitiello L. et al., *Front. Physiol.* 2018, 9, Article 1087).

It has been shown that SSAO/VAP-1 blocking by enzyme inhibitors has a pronounced effect in neutrophil-driven animal models of inflammation (Schilter H. C. et al., *Respir. Res.* 2015, 16, 42). Unregulated neutrophil activation and activity can lead to release of excessive myeloperoxidase (MPO) which reacts with hydrogen peroxide to form hypochlorous acid that causes local tissue damage and further inflammation. Given the co-localisation of MAO-B and SSAO/VAP-1 in several organs (heart, lung, muscle), inhibitors of both enzymes may be effective in treating diseases where neutrophils are implicated and oxidative stress is present.

Neutrophils have become the focus of new therapeutic approaches to the treatment of muscular dystrophies. Studies in mdx mice suggest that they promote muscle lesion; antibody-mediated depletion of host neutrophils in dystrophic mice resulted in a delayed and significantly reduced amount of skeletal muscle breakdown (Hodgetts S. et al., *Neuromuscular Disorders* 2006, 16, 591-602). Additionally, it has been shown that neutrophil elastase activity is increased in dystrophic mice and this increase impairs myoblast survival (Arecco, N. et al., *Sci. Rep.* 2016, 6, Article 24708). SSAO/VAP-1 is up-regulated in muscle donor tissue from DMD patients, and pharmacological inhibition of SSAO/VAP-1 activity in vivo reduces inflammation in mdx mice (WO 2015/189534, WO 2017/017414), further supporting the theory that neutrophils, recruited at least in part through SSAO-mediated activity, are involved in the progression of muscular dystrophy.

Current standard of care for patients suffering from DMD are the use of glucocorticoids such as prednisolone and deflazacort. Long term use of these steroids is associated with a high burden of side effects such as immunosuppression, obesity, insulin resistance and behavioural issues.

Both MAO and SSAO/VAP-1 activity are increased in obese dogs on a high-fat diet (Wenecq, E., et. al., *J. Physiol. Biochem.* 2006, 62, 113-124). Substrates of SSAO/VAP-1 have been shown to be lipolytic, and inhibition of SSAO/VAP-1 can stimulate lipolysis (Romauch, M., *Open Biology*, 2020, 10, Article 190035). Mice with a brain-specific knock-out of the insulin receptor (NIRKO mice) exhibit brain mitochondrial dysfunction with reduced mitochondrial oxidative activity, increased levels of reactive oxygen species, and increased levels of lipid and protein oxidation in the striatum and nucleus accumbens. NIRKO mice also exhibit increased levels of monoamine oxidase A and B (MAO A and B) leading to increased dopamine turnover in these areas. Studies in cultured neurons and glia cells indicate that these changes in MAO A and B are a direct consequence of loss of insulin signaling, and lead to behavioural disorders (Kleinridders, A. et. al., *PNAS*, 2015, 112, 3463-3468).

In diseases associated with reduced dopamine levels such as Parkinson's disease, Alzheimer's disease, attention deficit hyperactivity disorder and schizophrenia, inhibition of MAO-B leads to an increase in dopaminergic neuron activation, thereby alleviating symptoms. Oxidative stress due to increased MAO activity, and the consequent increased formation of $H_2O_2$ by MAO-B, plays a role in the degenerative processes associated with old age and Alzheimer's and Parkinson's diseases. Oxidative stress is also recognised as an important factor in the progression of Huntington's disease, where it has been shown that MAO-B is upregulated in the basal ganglia and pons in sufferers of the disease (Richards G., et. al., *Brain Res.* 2011, 1370, 204-214). MAO-B inhibitors used in neuromuscular and neurodegenerative diseases may therefore act by both elevating the levels of monoamines in the brain and reducing the formation of reactive oxygen species.

Inflammation linked to SSAO/VAP-1 enzyme activity is also believed to be an important feature of neuroinflammatory diseases such as Parkinson's disease, Alzheimer's disease and multiple sclerosis, and is a feature of the pathophysiology that occurs after a cerebral occlusion/reperfusion event (Aktas, O., et al., *Arch Neurol.* 2007, 64, 185-189). Excessive SSAO/VAP-1 activity has been independently implicated in these processes (Xu, H-L., et al., *J. Pharm.*

Exp. Ther., 2006, 317, 19-26). Pharmacological inhibition of SSAO/VAP-1 activity has been shown to reduce neutrophil infiltration into the brain, and reduce microglial activation in an LPS-induced model of neuroinflammation (Becchi et al., Br. J. Pharmacol. 2017, 174, 2302-2317). It is also thought that endothelial SSAO/VAP-1 plays a role in the cerebral amyloid angiopathy related to Alzheimer's disease through an effect on cerebrovascular amyloid-beta (Aβ) deposits (Sole M. et al., Neurobiology of Ageing 2015, 36, 762), leading to the underlying blood-brain barrier dysfunction associated with disease progression (Sole M. et. al., Biochim. Biophys. Acta. Mol. Basis. Dis. 2019, 1865, 2189-2202). Additionally, SSAO/VAP-1 oxidation of primary amines (such as methylamine to formaldehyde) has been linked to oxidative stress in models of Alzheimer's disease (Somfai G. M. et al., Neurochem Int. 2006, 48, 746-52).

The enzyme activity of MAO-B has been shown to play a role in vascular dysfunction. MAO-B-/- mice have preserved mitochondrial dysfunction (reduced oxidative stress), reduced fibrosis and apoptosis and preserved left ventricular function compared to WT mice when subjected to pressure overload induced by transverse aortic constriction (TAC) (Sturza A. et al., Hypertension 2013, 62, 140-6 & Kaluderic N. et al., Antioxid. Redox Signal. 2014, 10, 267-280). SSAO/VAP-1 is also strongly indicated in cardiovascular and metabolic disease, along with a pronounced role in inflammation and fibrosis in multiple organs including the lung, liver and kidney (Salmi M. & Jalkenen S. Antioxid. & Redox Signal. 2017, 30, 314-332).

MAO-B and SSAO/VAP-1 have significant overlap in several fields of research. They share a common oxidative pathway that can induce local and systemic oxidative stress which has implications in fibrosis, inflammation and cardiovascular disease. In muscular dystrophies, both targets are present in significant quantities in the muscle tissue and appear to play a role in both inflammatory and oxidative stress pathways in the progression of DMD, the most well-studied of these disorders. The potential beneficial effects of inhibiting these targets in terms of the systemic inflammation, fibrosis and cardiovascular deterioration is also clear. In the CNS they have complimentary roles where SSAO/VAP-1 can affect the infiltration/migration of leukocytes into the microvasculature and MAO-B can impact on neurodegeneration. Both of these actions are thought to have a significant effect on CNS-associated neuromuscular disorders, especially those with associated neuroinflammation, such as Parkinson's disease, Alzheimer's disease and multiple sclerosis, and further suggest promise for a therapeutic intervention of both enzymatic activities.

Given the complicity of MAO-B and SSAO/VAP-1 in the aforementioned diseases, a potent and selective inhibitor of both of these enzymes (dual inhibitor) could translate to a clear and significant therapeutic benefit in these neuromuscular, neuroinflammatory and neurodegenerative diseases.

Some known MAO inhibitors also inhibit SSAO/VAP-1 (e.g. the haloallylamine MAO inhibitor Mofegiline illustrated below (Milczek E. M. et. al. J. Med. Chem. 2008, 51, 8019-8026). Fluoroallylamine inhibitors are also described in U.S. Pat. No. 4,454,158 as MAO inhibitors.

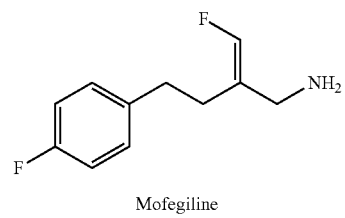 [SMILES: NC/C(=C/F)CCc1ccc(F)cc1]

Mofegiline

Other examples structurally related to Mofegiline, such as LJP1586, are described in WO 2007/120528:

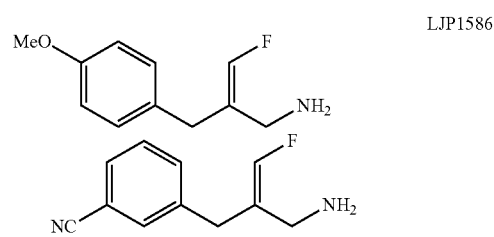

Additionally, a series of 2-substituted-3-haloallylamine SSAO/VAP-1 inhibitors has been disclosed in patent application WO 2013/163675 including PXS-4728 and PXS-4681:

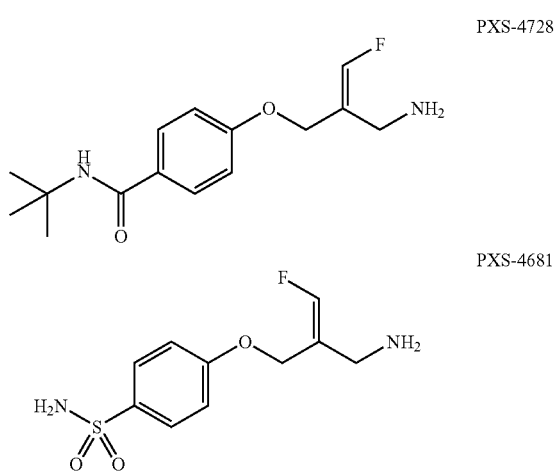

In both of these patent applications the enzyme inhibition reported was selective for SSAO/VAP-1 over all other amine oxidases, including MAO-B.

Recent patent applications describe aryloxy and heteroaryloxy 2-substituted-3-fluoroallylamines as SSAO/VAP-1 inhibitors (WO 2018/233633, WO 2018/151985, WO 2019/129213, WO 2019/241751 and WO 2020/063854). No MAO-A or MAO-B inhibitory data was disclosed.

Further patent applications for related SSAO/VAP-1 inhibitors report limited data for both MAO-B and MAO-A (WO 2018/196677, WO 2019/101086, WO 2019/024924, WO 2020/006177, WO 2020/063696, WO 2020/069335 and WO 2021/083209). None of the exemplified compounds presented therein have a reported $IC_{50}$ of <100 nM against the recombinant human form of MAO-B in a standard biochemical assay, and would therefore not be considered to be potent inhibitors of MAO-B.

Benzoxazole-based 2-substituted-3-fluoroallylamine SSAO/VAP-1 inhibitors have also been disclosed that show potency for inhibiting MAO-B ($IC_{50}$<0.1 μM) and lower potency for inhibiting MAO-A ($IC_{50}$ between 10-30 μM) (WO 2020/069330), such as the example shown below.

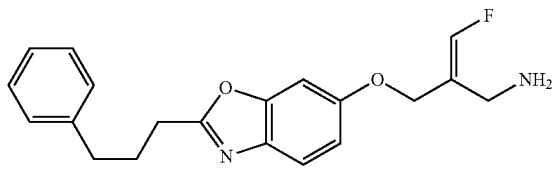 [SMILES: NC/C(=C\F)COc1ccc2nc(CCCc3ccccc3)oc2c1]

2-substituted-3-fluoroallylamine SSAO/VAP-1 inhibitors with direct attachment to the nitrogen of a five-membered heterocycle have also been described (WO 2019/180644). Activity for MAO-B and selectivity over MAO-A is reported for some of the exemplified compounds.

Relevant to the invention presented herein, the following compounds have been reported as selective SSAO/VAP-1 inhibitors and data is reported that shows that they are not potent inhibitors of MAO-B (CN 2019/109251166).

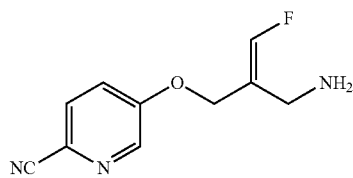

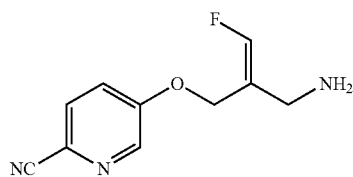

The present invention provides 2-substituted-3-fluoroallylamine compounds that are potent inhibitors of both SSAO/VAP-1 and MAO-B with particularly high selectivity over MAO-A. Surprisingly, modification of 2-phenoxymethylene-3-fluoroallylamine structures described previously has led to the development of novel compounds that are potent inhibitors of the human forms of both SSAO/VAP-1 and MAO-B enzymes, with high selectivity over inhibition of the MAO-A enzyme and consequently a favourable safety profile. In addition, the compounds of the invention have excellent pharmacokinetic properties and favourable safety profiles in vitro.

The present invention describes the synthesis and use of compounds which inhibit the amine oxidase activity of SSAO/VAP-1 and MAO-B, and describes the utility of such inhibitors to treat patients suffering from (but not limited to) neuromuscular disorders.

A first aspect of the invention provides for a compound of Formula I:

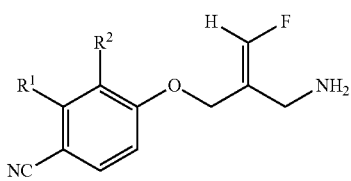

Formula 1 or a pharmaceutically acceptable salt, polymorphic form or solvate thereof; wherein:
$R^1$ is selected from the group consisting of hydrogen, fluorine, bromine and methyl; and
$R^2$ is hydrogen or fluorine.

A second aspect of the invention provides for a pharmaceutical composition comprising a compound according to the first aspect of the invention, or a pharmaceutically acceptable salt or solvate thereof, and at least one pharmaceutically acceptable excipient, carrier or diluent.

A third aspect of the invention provides for a method of inhibiting the amine oxidase activity of SSAO/VAP-1 and MAO-B in a subject in need thereof, comprising administering to the subject an effective amount of a compound according to the first aspect of the invention, or a pharmaceutically acceptable salt or solvate thereof, or a pharmaceutical composition according to the second aspect of the invention.

A fourth aspect of the invention provides for a method of treating or preventing a disease or disorder by inhibiting the activity of the SSAO/VAP-1 protein and the MAO-B protein, comprising administering to a subject in need thereof a therapeutically effective amount of a compound according to the first aspect of the invention or a pharmaceutically acceptable salt or solvate thereof, or a pharmaceutical composition according to the second aspect of the invention.

A fifth aspect of the invention provides for use of a compound according to the first aspect of the invention, or a pharmaceutically acceptable salt or solvate thereof, for the manufacture of a medicament for treating or preventing a disease or disorder by inhibiting the activity of the SSAO/VAP-1 protein and the MAO-B protein.

A sixth aspect of the invention provides for a compound according to the first aspect of the invention, or a pharmaceutically acceptable salt or solvate thereof, for use in treating or preventing a disease or disorder by inhibiting the activity of the SSAO/VAP-1 protein and the MAO-B protein.

In one embodiment of the methods and uses of the present invention the disease or disorder is ameliorated by the selective inhibition of SSAO/VAP-1 and MAO-B relative to MAO-A.

In one embodiment of the methods and uses of the present invention the disease is a neuromuscular disease.

In another embodiment of the invention the disease is a neuroinflammatory or a neurodegenerative disease.

Contemplated herein is combination therapy in which the methods further comprise co-administering additional therapeutic agents that are used for the treatment of neuromuscular, neuroinflammatory and neurodegenerative diseases.

Definitions

The following are some definitions that may be helpful in understanding the description of the present invention. These are intended as general definitions and should in no way limit the scope of the present invention to those terms alone, but are put forth for a better understanding of the following description.

Unless the context requires otherwise or specifically states to the contrary, integers, steps, or elements of the invention recited herein as singular integers, steps or elements clearly encompass both singular and plural forms of the recited integers, steps or elements.

Throughout this specification, unless the context requires otherwise, the word "comprise", or variations such as "comprises" or "comprising", will be understood to imply the inclusion of a stated step or element or integer or group of steps or elements or integers, but not the exclusion of any other step or element or integer or group of elements or integers. Thus, in the context of this specification, the term "comprising" means "including principally, but not necessarily solely".

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention includes within its scope isotopes of different atoms. Any atom not specifically designated as a particular isotope is meant to represent any stable isotope of that atom. Thus, the present disclosure should be understood to include deuterium and tritium isotopes of hydrogen.

All references cited in this application are specifically incorporated by cross-reference in their entirety. Reference to any such documents should not be construed as an admission that the document forms part of the common general knowledge or is prior art.

In the context of this specification the term "administering" and variations of that term including "administer" and "administration", includes contacting, applying, delivering or providing a compound or composition of the invention to an organism, or a surface by any appropriate means. In the context of this specification, the term "treatment", refers to any and all uses which remedy a disease state or symptoms, prevent the establishment of disease, or otherwise prevent, hinder, retard, or reverse the progression of disease or other undesirable symptoms in any way whatsoever.

In the context of this specification the term "effective amount" includes within its meaning a sufficient but non-toxic amount of a compound or composition of the invention to provide a desired effect. Thus, the term "therapeutically effective amount" includes within its meaning a sufficient but non-toxic amount of a compound or composition of the invention to provide the desired therapeutic effect. The exact amount required will vary from subject to subject depending on factors such as the species being treated, the sex, age and general condition of the subject, the severity of the condition being treated, the particular agent being administered, the mode of administration, and so forth. Thus, it is not possible to specify an exact "effective amount". However, for any given case, an appropriate "effective amount" may be determined by one of ordinary skill in the art using only routine experimentation.

DETAILED DESCRIPTION

Figure 1:
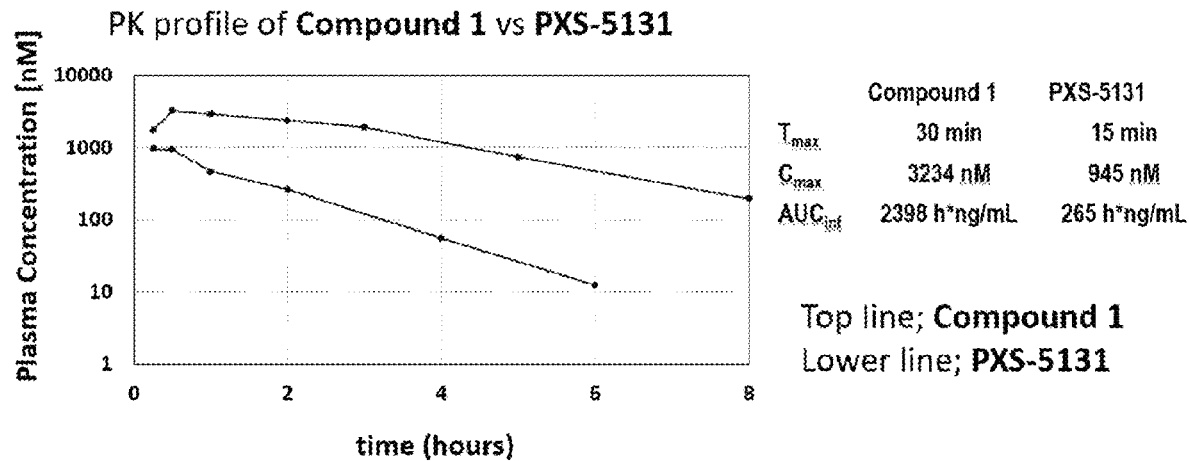
FIG. 1 depicts the pharmacokinetic time course in Wistar rats of PXS-5131 vs Compound 1.

The present invention relates to substituted haloallylamine derivatives which may inhibit both SSAO/VAP-1 and MAO-B. In particular, the present invention relates to substituted and unsubstituted 4-((2-(aminomethyl)-3-fluoroallyl)oxy)benzonitrile derivatives.

In particular, the present invention relates to a compound of Formula I:

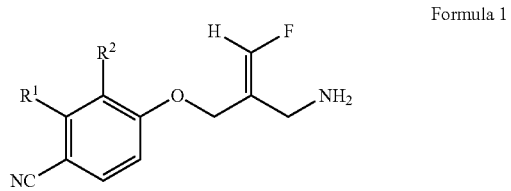

Formula 1 or a pharmaceutically acceptable salt, polymorphic form or solvate thereof; wherein:

$R^1$ is selected from the group consisting of hydrogen, fluorine, bromine and methyl; and $R^2$ is hydrogen or fluorine.

In one embodiment of compounds of the invention $R^1$ is hydrogen. In another embodiment of compounds of the invention $R^1$ is fluorine. In a further embodiment of compounds of the invention $R^1$ is bromine. In another embodiment of the compounds of the invention IV is methyl.

In one embodiment of compounds of the invention $R^2$ is hydrogen. In another embodiment of compounds of the invention $R^2$ is fluorine.

In one embodiment of compounds of the present invention $R^1$ is hydrogen and $R^2$ is hydrogen. In another embodiment of the compounds of the present invention $R^1$ is fluorine and $R^2$ is hydrogen. In a further embodiment of compounds of the invention $R^1$ is bromine and $R^2$ is hydrogen. In another embodiment of compounds of the present invention $R^1$ is hydrogen and $R^2$ is fluorine. In a further embodiment of compounds of the present invention $R^1$ is methyl and $R^2$ is hydrogen.

In one embodiment the compounds of the present invention are used as their free base. In another embodiment of the compounds of the present invention the compounds are used as pharmaceutically acceptable salts. In one embodiment of the compounds of the present invention the compounds are hydrochloride salts.

In one embodiment the compounds of the present invention are potent inhibitors of SSAO/VAP-1 and MAO-B. According to the present invention, a potent inhibitor of SSAO/VAP-1 has an $IC_{50}$ of less than 50 nM or less than 40 nM or less than 30 nM or less than 20 nM. In one embodiment a potent inhibitor of SSAO/VAP-1 has an $IC_{50}$ of less than 10 nM. According to the present invention, a potent inhibitor of MAO-B has an $IC_{50}$ of less than 250 nM or less than 200 nM or less than 150 nM or less than 100 nM. In one embodiment a potent inhibitor of MAO-B has an $IC_{50}$ of less than 50 nM.

In one embodiment the compounds of the present invention are potent inhibitors of both SSAO/VAP-1 and MAO-B with particularly high selectivity over MAO-A. The compounds of the present invention inhibit MAO-A with an $IC_{50}$ greater than 3000 nM or greater than 10000 nM, or greater than 20000 nM. In one embodiment the compounds of the present invention inhibit MAO-A with an $IC_{50}$ greater than 30000 nM.

The compounds of the present invention are selective inhibitors of SSAO/VAP-1 and MAO-B over MAO-A. The determination of relative selectivity for a given compound of MAO-B inhibition is defined as the relative ratio of the (MAO-A $IC_{50}$ value/MAO-B $IC_{50}$ value) is at least 12. The relative ratio of the (MAO-A $IC_{50}$ value/SSAO/VAP-1 $IC_{50}$ value) is at least 60. In another embodiment, for a given compound, the relative ratios of the (MAO-A $IC_{50}$ value/MAO-B $IC_{50}$ value) is at least 120 or is at least 600. In another embodiment, for a given compound, the relative ratios of the (MAO-A $IC_{50}$ value/SSAO/VAP-1 $IC_{50}$ value) is at least 300 or is at least 600 or is at least 3000.

In the context of the present disclosure, any one or more aspect(s) or embodiment(s) may be combined with any other aspect(s) or embodiment(s).

Exemplary compounds according to the present invention include the compounds set forth in TABLE 1:

TABLE 1

| Compound no. | Structure | Chemical name |
|---|---|---|
| 1 | (structure) | (E)-4-((2-(aminomethyl)-3-fluoroallyl)oxy)benzonitrile |
| 2 | (structure) | (E)-4-((2-(aminomethyl)-3-fluoroallyl)oxy)-2-fluorobenzonitrile |
| 3 | (structure) | (E)-4-((2-(aminomethyl)-3-fluoroallyl)oxy)-2-bromobenzonitrile |
| 4 | (structure) | (E)-4-((2-(aminomethyl)-3-fluoroallyl)oxy)-3-fluorobenzonitrile |

TABLE 1-continued

| Compound no. | Structure | Chemical name |
|---|---|---|
| 5 | ![structure] | (E)-4-((2-(aminomethyl)-3-fluoroallyl)oxy)-2-methylbenzonitrile |

Preparation of Compounds of Formula I

Compounds of Formula I described herein are synthesized using standard synthetic chemistry techniques using methods known in the art. The methods described are provided for illustrative purposes only and do not limit the scope of the claims provided herein.

Standard synthetic chemistry techniques are described in, but not limited to, Advanced Organic Chemistry, 8th Edition by March, John Wiley and Sons Inc. Standard procedures for the use of protecting groups for the temporary protection of functional groups such as alcohols, amines and carboxylic acids are described in for example Protecting Groups in Organic Synthesis, 5th Edition, John Wiley and Sons Inc.

Alternative reaction conditions for the chemical transformations described herein may be employed such as variation in solvent, reaction temperature, reaction time as well as different chemical reagents. Unless stated otherwise, starting materials for chemical synthesis and biological applications are available from commercial sources.

In general Schemes 1 and 2, P is a group used to protect a nitrogen functionality. Examples of P are carbonates such as the tert-butyloxycarbonyl (Boc), the 9-fluorenylmethyloxycarbonyl (FMOC), and the benzyloxycarbonyl (CBZ) groups. In some embodiments, hydroxybenzonitrile of Formula II (Scheme 1) is treated with an allyl bromide of Formula III in the presence of a suitable base using a suitable polar solvent at a temperature between 0° C. and 40° C. for several hours (Method A). In some embodiments, the base is potassium carbonate ($K_2CO_3$) or alternatively cesium carbonate ($Cs_2CO_3$) In another embodiment, the base is sodium hydride (NaH). In some embodiments, the solvent is dimethylformamide (DMF) or alternatively acetone. In another embodiment, the solvent is acetonitrile. Following standard extraction and purification methods the product described by Formula IV can be obtained in good yield and purity.

Scheme 1

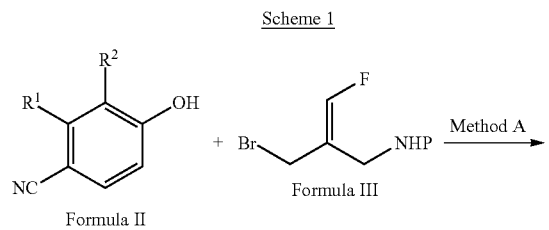

In some embodiments, fluorobenzonitrile of Formula V (Scheme 2) is treated with allylic alcohol of Formula VI in the presence of a suitable base using a suitable solvent at a temperature between 0° C. and 40° C. for several minutes (Method C). In one embodiment, the base is NaH. In another embodiment, the solvent is tetrahydrofuran (THF) or, alternatively, DMF. Following standard extraction and purification methods the product described by Formula IV can be obtained in good yield and purity.

Scheme 2

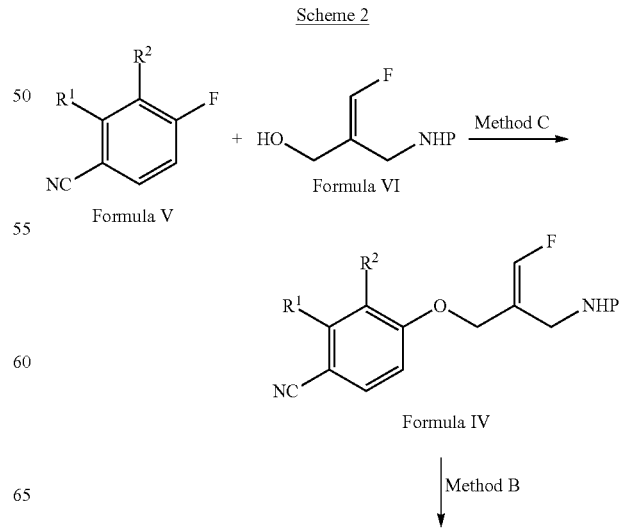

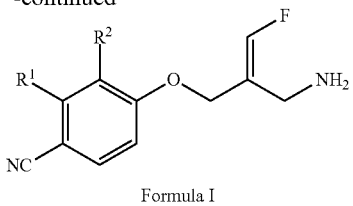

Formula I

There are many, well established, chemical procedures for the deprotection of the compounds described by Formula IV to the compounds described by Formula I (Method B; Schemes 1 and 2). For example, if P is a Boc protecting group, compounds described by Formula IV can be treated with an acidic reagent such as dry hydrogen chloride in a solvent such as diethyl ether or dioxane to furnish the compounds described by Formula I as the hydrochloride salts. In another embodiment, the acidic reagent is trifluoroacetic acid (TFA). In one embodiment the compounds of Formula I may be used as the free base. In general, the free base compounds are converted to acid addition salts for ease of handling and for improved chemical stability. Examples of acid addition salts include but are not limited to hydrochloride, hydrobromide, 2,2,2-trifluoroacetate and methanesulfonate salts.

Therapeutic Uses

The present invention provides methods for the use of compounds described by Formula I to inhibit membrane-bound SSAO/VAP-1 and soluble SSAO/VAP-1. In addition, the present invention provides methods for the use of compounds described by Formula I to inhibit MAO-B. The relative inhibitory potencies of the compounds can be determined by the amount needed to inhibit the amine oxidase activity of SSAO/VAP-1 and MAO-B in a variety of ways, e.g., in an in vitro assay with recombinant human protein or with recombinant non-human enzyme, in cellular assays expressing normal rodent enzyme, in cellular assays which have been transfected with human protein, in in vivo tests in rodent and other mammalian species, and the like.

The present invention also discloses methods to use the compounds described by Formula I to inhibit SSAO/VAP-1 and MAO-B in patients suffering from a neuromuscular disease, and methods to treat the symptoms associated with neuromuscular diseases.

Thus, in one aspect, the present invention is directed to a method of inhibiting the amine oxidase enzyme activity of SSAO/VAP-1 and MAO-B in a subject in need thereof, comprising administering to the subject an effective amount of a compound of Formula I, or a pharmaceutically acceptable salt or solvate thereof, or a pharmaceutical composition thereof.

In another aspect, the present invention is directed to a method of treating or preventing a disease or disorder by inhibiting the activity of the SSAO/VAP-1 protein and the MAO-B protein, comprising administering to a subject in need thereof a therapeutically effective amount of a compound of Formula I, or a pharmaceutically acceptable salt or solvate thereof, or a pharmaceutical composition thereof. In one embodiment the present invention is directed to a method of treating a disease or disorder by inhibiting the activity of the SSAO/VAP-1 protein and the MAO-B protein. In another embodiment the present invention is directed to a method of preventing a disease or disorder by inhibiting the activity of the SSAO/VAP-1 protein and the MAO-B protein.

In still another aspect, the present invention is directed to methods of treating a disease or disorder modulated by SSAO/VAP-1 and MAO-B, said methods comprising administering to a subject in need thereof a therapeutically effective amount of a compound of Formula I, or a pharmaceutically acceptable salt or solvate thereof, or a pharmaceutical composition thereof.

In a further aspect, the present invention is directed to a method of treating or preventing a disease or disorder selected from the group consisting of a neuromuscular disorder, a neurodegenerative disease or a neuroinflammatory disease, the method comprising administering to a subject in need thereof a therapeutically effective amount of a compound of Formula I, or a pharmaceutically acceptable salt or solvate thereof, or a pharmaceutical composition thereof. In one embodiment the present invention is directed towards treating a disease or disorder selected from the group consisting of a neuromuscular disorder, a neurodegenerative disease or a neuroinflammatory disease. In another embodiment the present invention is directed towards preventing a disease or disorder selected from the group consisting of a neuromuscular disorder, a neurodegenerative disease or a neuroinflammatory disease.

Another embodiment of the present invention is a method of treatment wherein the disease or disorder is ameliorated by the selective inhibition of SSAO/VAP-1 and MAO-B relative to MAO-A. By selectively inhibiting SSAO/VAP-1 and MAO-B relative to MAO-A, the compounds of the present invention provide a favourable safety profile.

A further aspect of the present invention provides for use of a compound of Formula I, or a pharmaceutically acceptable salt or solvate thereof, for the manufacture of a medicament for treating or preventing a disease or disorder by inhibiting the activity of the SSAO/VAP-1 protein and the MAO-B protein.

Another aspect of the present invention provides for use of a compound of Formula I, or a pharmaceutically acceptable salt or solvate thereof, for the manufacture of a medicament for treating or preventing a disease or disorder selected from the group consisting of a neuromuscular disorder, a neurodegenerative disease or a neuroinflammatory disease.

The above-described methods and uses are applicable wherein the disease is a neuromuscular disorder. As employed herein "neuromuscular disorder or disease" covers disorders that impair the functioning of the muscles, either directly, being pathologies of the voluntary muscle, or indirectly, being pathologies of nerves or neuromuscular junctions. This description encompasses a wide range of disorders including muscular dystrophies such as; Duchenne muscular dystrophy (DMD), Becker muscular dystrophy, Emery-Dreifuss muscular dystrophy, facioscapulohumeral muscular dystrophy, limb-girdle muscular dystrophy, myotonic dystrophy, oculopharyngeal muscular dystrophy and congenital muscular dystrophies; and also indirect, central disorders such as; Parkinson's disease, multiple sclerosis, Huntington's disease and Creutzfeldt-Jakob disease. In one embodiment of the methods and uses of present invention the muscular dystrophy is selected from the group consisting of Duchenne muscular dystrophy (DMD), Becker muscular dystrophy, facioscapulohumeral muscular dystrophy and myotonic dystrophy. In one embodiment of the methods and uses of present invention the muscular dystrophy is Duchenne muscular dystrophy (DMD).

The term "neuromuscular disease" can also be used to refer to motor neuron diseases, such as amyotrophic lateral sclerosis and spinal muscular atrophy, ion channel diseases, myopathies, mitochondrial diseases, such as Friedreich's ataxia, neuromuscular junction diseases, such as myasthenia gravis, and peripheral nerve diseases, such as Charcot-Marie-Tooth disease.

The dual benefits of SSAO/VAP-1 and MAO-B inhibition have the potential to treat inflammatory disorders related to oxidative stress.

As employed herein, "inflammation or inflammatory disorders" embraces a wide variety of indications, including arthritis (including juvenile rheumatoid arthritis), Crohn's disease, ulcerative colitis, inflammatory bowel diseases (e.g., irritable bowel disease), psoriasis, asthma, pulmonary inflammation, COPD, bronchiectasis, skin inflammation, ocular disease, contact dermatitis, liver inflammation, liver autoimmune diseases, autoimmune hepatitis, primary biliary cirrhosis, sclerosing cholangitis, autoimmune cholangitis, alcoholic liver disease, artherosclerosis, chronic heart failure, congestive heart failure, ischemic diseases, stroke and complications thereof, inflammation arriving from bacterial infection such as those experienced in sepsis, acute lung injury and cystic fibrosis, myocardial infarction and complications thereof, inflammatory cell destruction following stroke, synovitis and systemic inflammatory sepsis.

Disease associated with the term "oxidative stress" covers disorders where an increase in reactive oxygen species has been linked to the disease progression or directly to the symptoms of the disease and includes a number of different diseases including cancer, muscular dystrophy, Alzheimer's disease, Parkinson's disease, diabetes, cardiovascular conditions such as high blood pressure, atherosclerosis and stroke, inflammatory disorders, chronic fatigue syndrome, fragile X syndrome, depression, attention deficit hyperactivity disorder, autism, Asperger syndrome, Huntington's disease, amyotrophic lateral sclerosis, multiple sclerosis, asthma and male infertility.

In one embodiment of the methods and uses of the present invention the disease is an inflammatory condition selected from a neurological disease, a metabolic disease and fibrosis.

The above-described methods and uses are also applicable wherein the disease is a neurological disease or disorder. As employed herein, "neurological disease or disorder" covers both neuroinflammatory and neurodegenerative diseases and embraces a variety of indications, including stroke, Alzheimer's disease, familial Alzheimer's disease, Parkinson's disease, senile dementia, vascular dementia, Huntington's disease, amyotrophic lateral sclerosis, multiple sclerosis, Down's syndrome and homozygotes for the apolipoprotein E4 allele. In one embodiment of the methods and uses of the present invention the neurodegenerative or neuroinflammatory disease is selected from the group consisting of Alzheimer's disease, Parkinson's disease, multiple sclerosis, Huntington's disease, amyotrophic lateral sclerosis, spinal muscular atrophy, myasthenia gravis and Charcot-Marie-Tooth disease.

Other examples of neurological disorders include psychiatric diseases, which include depression, anxiety, panic attack, social phobia, schizophrenia, anorexia and depressive mood disorder.

Further examples of neurological disorders include withdrawal syndromes induced by alcohol, nicotine and other addictive drugs.

The above described methods and uses are also applicable wherein the disease is a metabolic disorder or disease. As employed here "metabolic disorder or disease" embraces a wide variety of indications, including such diseases as obesity, Type 1 and 2 diabetes, hypertension, atherosclerosis, high blood pressure, chronic kidney disease, dyslipidemias, heart disease, metabolic syndrome, insulin resistance, diabetic nephropathy, glomerulosclerosis, diabetic retinopathy, choroidal neovascularization and cardiovascular complications arising as a result thereof.

In accordance with yet another aspect of the present invention, there are provided methods for treating patients suffering from Type 1 and 2 diabetes, and diabetes-related diseases with a dual SSAO/VAP-1 and MAO-B inhibitor. Diabetes-related diseases contemplated for treatment herein include diabetic nephropathy, diabetic macular oedema, glomerulosclerosis, diabetic retinopathy, choroidal neovascularization and cardiovascular complications arising as a result thereof.

The above described methods and uses are also applicable wherein the disease is fibrosis. As employed here "fibrosis" includes such diseases as cystic fibrosis, idiopathic pulmonary fibrosis, kidney fibrosis, chronic obstructive pulmonary disease, pleural fibrosis and radiation-induced pulmonary fibrosis, non-diabetic renal fibrosis, pancreatic fibrosis, scleroderma, connective tissue diseases, scarring, skin fibrosis, fibrosis associated with organ transplant, stenosis, liver fibrosis, including alcoholic liver disease, fatty liver disease, non-alcoholic steatohepatitis, acute and chronic hepatitis, biliary cirrhosis, primary sclerosing cholangitis, hepatocellular carcinoma and toxic liver injury, and other diseases where excessive fibrosis contributes to disease pathology. In one embodiment the fibrosis is cardiac fibrosis.

Pharmaceutical and/or Therapeutic Formulations

In another embodiment of the present invention, there are provided compositions comprising a compound having Formula I and at least one pharmaceutically acceptable excipient, carrier or diluent thereof. The compound(s) of Formula I may also be present as suitable salts, including pharmaceutically acceptable salts.

The phrase "pharmaceutically acceptable carrier" refers to any carrier known to those skilled in the art to be suitable for the particular mode of administration. In addition, the compounds may be formulated as the sole pharmaceutically active ingredient in the composition or may be combined with other active ingredients.

The phrase "pharmaceutically acceptable salt" refers to any salt preparation that is appropriate for use in a pharmaceutical application. By pharmaceutically acceptable salt it is meant those salts which, within the scope of sound medical judgement, are suitable for use in contact with the tissues of humans and lower animals without undue toxicity, irritation, allergic response and the like, and are commensurate with a reasonable benefit/risk ratio.

Pharmaceutically acceptable salts are well known in the art and include acid addition and base salts. Hemisalts of acids and bases may also be formed. Pharmaceutically acceptable salts include amine salts of mineral acids (e.g., hydrochlorides, hydrobromides, sulfates, and the like); and amine salts of organic acids (e.g., formates, acetates, lactates, malates, tartrates, citrates, ascorbates, succinates, maleates, butyrates, valerates, fumarates, and the like).

For compounds of Formula I having a basic site, suitable pharmaceutically acceptable salts may be acid addition salts. For example, suitable pharmaceutically acceptable salts of such compounds may be prepared by mixing a pharmaceutically acceptable acid such as hydrochloric acid, sulfuric acid, methanesulfonic acid, succinic acid, fumaric acid, maleic acid, benzoic acid, phosphoric acid, acetic acid, oxalic acid, carbonic acid, tartaric acid, or citric acid with the compounds of the invention.

S. M. Berge et al. describe pharmaceutically acceptable salts in detail in *J. Pharmaceutical Sciences,* 1977, 66:1-19. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphorsulfonate, citrate, digluconate, cyclopentanepropionate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Suitable base salts are formed from bases that form non-toxic salts.

Pharmaceutically acceptable salts of compounds of Formula I may be prepared by methods known to those skilled in the art, including for example:

i. by reacting the compound of formula I with the desired acid or base;
ii. by removing an acid- or base-labile protecting group from a suitable precursor of the compound of formula I or by ring-opening a suitable cyclic precursor, for example, a lactone or lactam, using the desired acid or base; or
iii. by converting one salt of the compound of formula I to another by reaction with an appropriate acid or base or by means of a suitable ion exchange column.

The above reactions (i)-(iii) are typically carried out in solution. The resulting salt may precipitate out and be collected by filtration or may be recovered by evaporation of the solvent. The degree of ionisation in the resulting salt may vary from completely ionised to almost non-ionised.

Thus, for instance, suitable pharmaceutically acceptable salts of compounds according to the present invention may be prepared by mixing a pharmaceutically acceptable acid such as hydrochloric acid, sulfuric acid, methanesulfonic acid, succinic acid, fumaric acid, maleic acid, benzoic acid, phosphoric acid, acetic acid, oxalic acid, carbonic acid, tartaric acid, or citric acid with the compounds of the invention. Suitable pharmaceutically acceptable salts of the compounds of the present invention therefore include acid addition salts.

The compounds of the invention may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when the solvent is water.

Compositions herein comprise one or more compounds provided herein. The compounds are, in one embodiment, formulated into suitable pharmaceutical preparations such as solutions, suspensions, tablets, creams, gels, dispersible tablets, pills, capsules, powders, sustained release formulations or elixirs, for oral administration or in sterile solutions or suspensions for parenteral administration, as well as transdermal patch preparation and dry powder inhalers. In one embodiment, the compounds described above are formulated into pharmaceutical compositions using techniques and procedures well known in the art (see, e.g., Ansel *Introduction to Pharmaceutical Dosage Forms, Fourth Edition* 1985, 126).

In the compositions, effective concentrations of one or more compounds or pharmaceutically acceptable derivatives thereof is (are) mixed with a suitable pharmaceutical carrier. The compounds may be derivatized as the corresponding salts, esters, enol ethers or esters, acetals, ketals, orthoesters, hemiacetals, hemiketals, acids, bases, solvates, hydrates or prodrugs prior to formulation, as described above. The concentrations of the compounds in the compositions are effective for delivery of an amount, upon administration, that treats, prevents, or ameliorates one or more of the symptoms of diseases or disorders to be treated.

In one embodiment, the compositions are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and in PCT publication WO 04/018997, and then extrapolated from there for dosages for humans.

The concentration of active compound in the pharmaceutical composition will depend on absorption, distribution, inactivation and excretion rates of the active compound, the physicochemical characteristics of the compound, the dosage schedule, and amount administered as well as other factors known to those of skill in the art.

In one embodiment, a therapeutically effective dosage should produce a serum concentration of active ingredient of from about 0.1 ng/mL to about 50-100 µg/mL. The pharmaceutical compositions, in another embodiment, should provide a dosage of from about 0.001 mg to about 2000 mg of compound per kilogram of body weight per day. Pharmaceutical dosage unit forms are prepared to provide from about 0.01 mg, 0.1 mg or 1 mg to about 500 mg, 1000 mg or 2000 mg, and in one embodiment from about 10 mg to about 500 mg of the active ingredient or a combination of essential ingredients per dosage unit form.

Dosing may occur at intervals of minutes, hours, days, weeks, months or years or continuously over any one of these periods. Suitable dosages lie within the range of about 0.1 ng per kg of body weight to 1 g per kg of body weight per dosage. The dosage is preferably in the range of 1 µg to 1 g per kg of body weight per dosage, such as is in the range of 1 mg to 1 g per kg of body weight per dosage. Suitably, the dosage is in the range of 1 µg to 500 mg per kg of body weight per dosage, such as 1 µg to 200 mg per kg of body weight per dosage, or 1 µg to 100 mg per kg of body weight per dosage. Other suitable dosages may be in the range of 1 mg to 250 mg per kg of body weight, including 1 mg to 10, 20, 50 or 100 mg per kg of body weight per dosage or 10 µg to 100 mg per kg of body weight per dosage.

Suitable dosage amounts and dosing regimens can be determined by the attending physician and may depend on the particular condition being treated, the severity of the condition, as well as the general health, age and weight of the subject.

In instances in which the compounds exhibit insufficient solubility, methods for solubilizing compounds may be used.

Such methods are known to those of skill in this art, and include, but are not limited to, using co-solvents, such as dimethylsulfoxide (DMSO), using surfactants, such as TWEEN®, dissolution in aqueous sodium bicarbonate, formulating the compounds of interest as nanoparticles, and the like. Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in one embodiment, formulated and administered in unit-dosage forms or multiple-dosage forms. The active ingredient may be administered at once, or may be divided into a number of smaller doses to be administered at intervals of time. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Actual methods of preparing such dosage forms are known, or will be apparent, to those skilled in this art; for example, see *Remington's Pharmaceutical Sciences*, Mack Publishing Company, Easton, Pa., 15th Edition, 1975.

Dosage forms or compositions containing active ingredient in the range of 0.005% to 100% (wt %) with the balance made up from non-toxic carrier may be prepared. Methods for preparation of these compositions are known to those skilled in the art. The contemplated compositions may contain 0.001%-100% (wt %) active ingredient, in one embodiment 0.1-95% (wt %), in another embodiment 75-85% (wt %).

Modes of Administration

Convenient modes of administration include injection (subcutaneous, intravenous, etc.), oral administration, inhalation, transdermal application, topical creams or gels or powders, vaginal or rectal administration. Depending on the route of administration, the formulation and/or compound may be coated with a material to protect the compound from the action of enzymes, acids and other natural conditions which may inactivate the therapeutic activity of the compound. The compound may also be administered parenterally or intraperitoneally.

Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

Solid Compositions for Oral Administration

In certain embodiments, the formulations are solid dosage forms, in one embodiment, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polvinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

The compound, or pharmaceutically acceptable derivative thereof, could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Liquid Compositions for Oral Administration

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Elixirs are clear, sweetened, aqueous or hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and ethanol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethyl-cellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is in one embodiment encapsulated in a gelatin capsule. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Injectables, Solutions and Emulsions

Parenteral administration, in one embodiment characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, olive oil, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylceluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation. These formulations for administration to the respiratory tract can be in the form of an aerosol or solution for a nebulizer, or as a microfine powder for insufflation, alone or in combination with an inert carrier such as lactose. In such a case, the particles of the formulation will, in one embodiment, have diameters of less than 50 microns, in one embodiment less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% (vol %) isotonic solutions, pH about 5-7, with appropriate salts.

Compositions for Other Routes of Administration

Other routes of administration, such as transdermal patches, including iontophoretic and electrophoretic devices, vaginal and rectal administration, are also contemplated herein.

Transdermal patches, including iontophoretic and electrophoretic devices, are well known to those of skill in the art. For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (*theobroma* oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm.

Tablets and capsules for rectal administration are manufactured using the same pharmaceutically acceptable substance and by the same methods as for formulations for oral administration.

Targeted Formulations

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions.

Co-Administration with Other Drugs

In accordance with another aspect of the present invention, it is contemplated that compounds of Formula I as described herein may be administered to a subject in need thereof in combination with medication considered by those of skill in the art to be current standard of care for the condition of interest. Such combinations provide one or more advantages to the subject, e.g., requiring reduced dosages to achieve similar benefit, obtaining the desired palliative effect in less time, and the like.

Compounds in accordance with the present invention may be administered as part of a therapeutic regimen with other drugs. It may desirable to administer a combination of active compounds, for example, for the purpose of treating a particular disease or condition. Accordingly, it is within the scope of the present invention that two or more pharmaceutical compositions, at least one of which contains a compound of Formula (I) according to the present invention, may be combined in the form of a kit suitable for co-administration of the compositions.

In one embodiment of the methods of the present inventions a compound of Formula I may be administered with a second therapeutic agent. In one embodiment the second therapeutic agent is selected from the group consisting of, an anti-inflammatory agent, an anti-hypertensive agent, an anti-fibrotic agent, an anti-angiogenic agent and an immunosuppressive agent.

In one embodiment of the methods of the present inventions a compound of Formula I may be administered with a second therapeutic agent selected from the group consisting of a steroidal anti-inflammatory agent like prednisolone and deflazacort, or a non-steroidal anti-inflammatory such as aspirin, paracetamol, ibuprofen, naproxen, indomethacin, celecoxib and diclofenac.

In another embodiment of the methods of the present inventions a compound of Formula I may be administered with a second therapeutic agent selected from the group consisting of a calcium channel blocker, such as verapamil, nisoldipine and amlodipine; an angiotensin II receptor antagonist, such as irbesartan, losartan, telmisartan and valsartan; and an inhibitor of angiotensin-converting enzyme, such as benazepril, captopril, enalapril and fosinopril.

In another embodiment of the methods of the present inventions a compound of Formula I may be administered with a second therapeutic agent selected from the group consisting of pirfenidone and nintedanib.

In another embodiment of the methods of the present inventions a compound of Formula I may be administered with a second therapeutic agent selected from the group consisting of axitinib, bevacizumab, everolimus, lenalidomide, regorafenib, sorafenib, sunitinib, thalidomide, vandetanib and zivaflibercept.

In another embodiment of the methods of the present inventions a compound of Formula I may be administered with a second therapeutic agent selected from the group consisting of a glucocorticoid, such as prednisone, dexamethasone, and hydrocortisone; a cyostatic agent, such as cyclophosphamide, azathioprine, dactinomycin and methotrexate; an antibody acting directly against an immune response, such as basiliximab, daclizumab and muromonab; agents that act upon the immunophilins, such as cyclosporine, rapamycin, tacrolimus and everolimus; and other immunosuppressant agents, including fingolimod, interferon therapy, infliximab, etanercept and adalimumab.

In one embodiment of the methods of the present inventions a compound of Formula I may be administered with a second therapeutic agent. In one embodiment the second therapeutic agent is selected from drugs thought to be useful in the treatment of muscular dystrophies, including; prednisone, deflazacort, ataluren, myostatin, eteplirsen, golodirsen, casimersen, idebenone, pamrevlumab, edasalonexent, givinostat, rimeporide and ifetroban.

When two or more active ingredients are co-administered, the active ingredients may be administered simultaneously, sequentially or separately. In one embodiment the compound of Formula I is co-administered simultaneously with a second therapeutic agent. In another embodiment the compound of Formula I and the second therapeutic agent are administered sequentially. In a further embodiment the compound of Formula I and the second therapeutic agent are administered separately.

The invention will now be described in greater detail, by way of illustration only, with reference to the following non-limiting examples. The examples are intended to serve to illustrate the invention and should not be construed as limiting the generality of the disclosure of the description throughout this specification.

For purposes of this specification, the following abbreviations have the indicated meanings:
rt=room temperature
min=minute(s)
h=hour(s)
NaHMDS=sodium hexamethyldisilazide
THF=tetrahydrofuran
DMF=dimethylformamide
NaO$^t$Bu=sodium tertbutoxide
TFA=trifluoroacetic acid
DIBAL=diisobutylaluminumhydride
MTBE=methyl tertbutylether
DIPEA=diisopropylethylamine
LC-MS=liquid chromatography-mass spectroscopy
rpm=revolutions per minute
NMR=nuclear magnetic resonance
DMSO=dimethylsulfoxide
Boc=tert-butyloxycarbonyl
HPLC=high-performance liquid chromatography (also, high pressure liquid chromatography)
rac.=racemic
TLC=thin-layer chromatography Experimental: General Methods All commercially available solvents and reagents were used as received. Where appropriate, reactions were carried out under an argon atmosphere. Reactions were monitored by either analytical thin-layer chromatography (TLC) or by analytical liquid chromatography-mass spectrometry (LC- MS) recorded on either a Shimadzu LC-MS 2020 instrument or an Agilent LC-MS 1200 instrument using reverse-phase conditions. Purification of intermediates and final compounds was conducted, where necessary, using column chromatography or preparative HPLC. Normal-phase column chromatography was conducted under medium pressure either on silica gel or on prepacked silica gel cartridges using a flash chromatography system (CombiFlash Rf200, Teledyne Isco systems, USA). Reverse-phase column chromatography was conducted under low pressure on prepacked C18 cartridges using a flash chromatography system (Reveleris® X2). Eluents were monitored by UV light (λ=254/280 nm). $^1$H-NMR and $^{19}$F-NMR spectra were recorded using either a Bruker 300 MHz NMR spectrometer or a Bruker Avance III plus 400 MHz NMR spectrometer. Chemical shifts (δ) are reported as parts per million (ppm) relative to tetramethylsilane (TMS; internal standard). The following abbreviations are used for multiplicities: s=singlet; br s=broad singlet; d=doublet; t=triplet; q=quartet; p=pentet; m=multiplet; and br m=broad multiplet. Low resolution mass spectra (MS) were obtained as electrospray-atmospheric pressure ionization (ES-API) mass spectra on a Shimadzu LC-MS 2020 or an Agilent LC-MS 1200 instrument. All animal experiments were conducted in compliance with institutional guidelines and approval from local ethics committees.

Example 1

Preparation of Tert-Butyl (E)-(2-(Bromomethyl)-3-Fluoroallyl)Carbamate (Int-6)

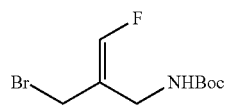

Procedure A: Preparation of Tert-Butyl 3-(2,5-Dimethyl-1H-Pyrrol-1-Yl)Propanoate (Int-1)

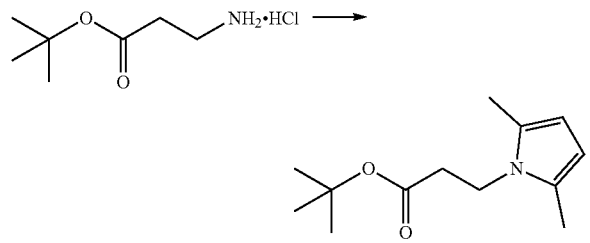

To a vessel charged with acetonitrile (754 L) under nitrogen was added sequentially β-alanine tert-butyl ester hydrochloride (75 kg), 2,5-hexanedione (97.5 L) and potassium carbonate (75 kg). The resulting mixture was heated to 75° C. over 2 h and then stirred for a further 4 h. The reaction mixture was cooled to 55° C. and then concentrated in vacuo to ~290 L. Water (1200 L) was then added to the residue at 55° C. The mixture was stirred at 55° C. for 1 h, and then cooled to 10° C. over 2 h. Stirring was continued at 10° C. for 10 h. The slurry was then centrifuged and the liquid phase removed. The resulting "cake" was rinsed with further water (150 L×3), centrifuging and removing the liquid phase after each rinsing cycle. After final removal of the filtrate, the wet "cake" was dried under vacuum at 40° C. for 24 h to afford Int-1 (79.4 kg, 85%). $^1$H-NMR (300 MHz, CDCl$_3$) δ ppm: 5.78 (s, 2H), 4.02-4.07 (m, 2H), 2.50-2.56 (m, 2H), 2.25 (s, 6H), 1.47 (s, 9H).

Procedure B: Preparation of 1-(Tert-Butyl) 3-Ethyl 2-(Difluoromethyl)-2-((2,5-Dimethyl-1H-Pyrrol-1-Yl)Methyl)Malonate (Int-2)

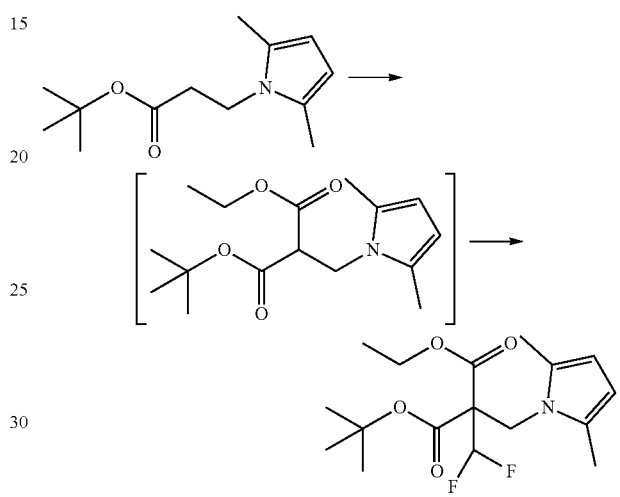

This process was performed on two batches of Int-1 (39.5 kg×2). The batches were combined at a late stage.

To vessel (A), charged with THF (277 L) under nitrogen was added NaHMDS (2.0 M; 245 kg) over 20 min. The resulting mixture was cooled to −58° C. To vessel (B), charged with THF (198 L) under nitrogen at −50° C. was added Int-1 (39.5 kg). The resulting mixture was stirred at −50° C. for 25 min. The contents of vessel (B) was then transferred to vessel (A) over 30 min at −58° C. To vessel (A) was then added ethyl chloroformate (17.4 L) over 1 h during which time an exotherm was observed. The resulting mixture was stirred at −58° C. for 1 h. To this was added NaO$^t$Bu (15.3 kg) over 15 min. Chlorodifluoromethane (17.8 kg) was then added slowly at −20° C. The mixture was stirred at −30° C. for 2 h. The vessel was then charged with further chlorodifluoromethane (7.00 kg) slowly at −20° C. Stirring was continued for a further 2 h at −20° C. The reaction vessel was charged with water (356 L) followed by citric acid (79 kg). The resulting mixture was stirred for 30 min and the organic layer separated. NaCl solution (10%, 342.4 kg) was added and the mixture stirred for 1 h. The organic layer was separated and concentrated in vacuo. Residue was dissolved in n-heptane (584.8 kg) and silica gel added. Stirred for 30 min and then filtered through Celite®, washing with n-heptane (434 kg). Combined filtrate was concentrated in vacuo and the residue thus obtained recrystallized from EtOH:H$_2$O (1:1) to afford the title compound, hit 2, as a light yellow solid (91.0 kg, 74.5%). $^1$H-NMR (300 MHz, CDCl$_3$) δ ppm: 6.29 (t, J=54.6 Hz, 1H), 0.72 (s, 2H), 4.56-4.69 (m, 2H), 4.12-4.23 (m, 1H), 3.98-4.08 (m, 1H), 2.20 (s, 6H), 1.36 (s, 9H), 1.23 (t, J=7.2 Hz, 3H).

Procedure C: Preparation of Ethyl (E)-2-((2,5-Dimethyl-1H-Pyrrol-1-Yl)Methyl)-3-Fluoroacrylate (Int-3)

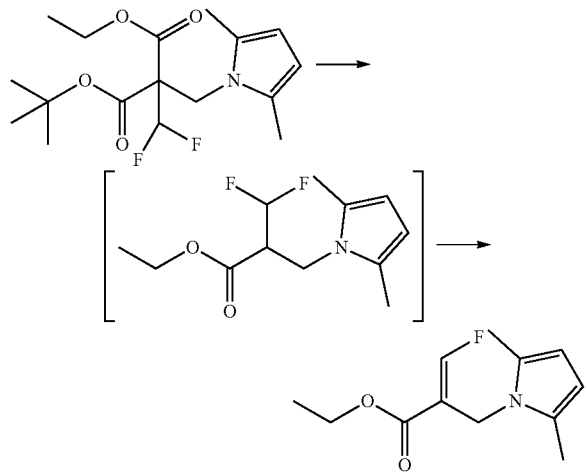

To reaction vessel (A), charged with TFA (279 L) at 10° C. under nitrogen was added Int-2 (91 kg). The resulting mixture was heated to 35° C., left to stir for 13 h and then cooled to 5° C. To reaction vessel (B) was added triethylamine (620 L) followed by n-heptane (532 L). The resulting solution was cooled to 5° C. The contents of reactor (A) was then transferred to reactor (B) over 2 h. The resulting mixture in reactor vessel (B) was heated to 40° C. and stirring was continued for 10 h. The reaction mixture was cooled to 10° C. and then washed with water (910 L). The organic phase was separated and washed with a solution of citric acid (91 kg) in water (455 L) followed by a solution of NaCl (73 kg) in water (410 L). To the organic phase was added silica gel (91 kg) and the resulting slurry was stirred for 30 min. The slurry was then filtered and the filter "cake" was washed with n-heptane. The filtrate was concentrated in vacuo and the resulting residue was taken up in toluene (520 L). After further concentration to 650-750 L, the resulting solution of crude Int-3 was used in the subsequent step. $^1$H-NMR (300 MHz, CDCl$_3$) δ ppm: 7.60 (d, J=80.1 Hz, 1H), 5.77 (s, 2H), 4.67-4.68 (m, 2H), 4.20 (q, J=7.2 Hz, 2H), 2.26 (s, 6H), 1.27 (t, J=7.2 Hz, 3H).

Procedure D: Preparation of (E)-2-((2,5-Dimethyl-1H-Pyrrol-1-Yemethyl)-3-Fluoroprop-2-En-1-Ol (Int-4)

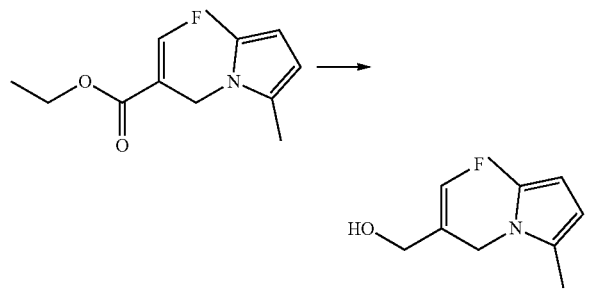

To the solution of Int-3 in toluene (520 L), prepared in the previous step, under nitrogen at −55° C. was added diisobutylaluminum hydride (DIBAL) (1.5 M in toluene; 199.2 kg) dropwise over 4 h. The resulting mixture was stirred at −45° C. for 1 h. IPC analysis after this time indicated incomplete conversion. A further amount of DIBAL (1.5 M in toluene; 15 kg) was added dropwise over 40 min at −55° C. The mixture was then stirred at −45° C. for a further 30 min and then warmed to 10° C. To quench the reaction, a cold (0° C.) solution of citric acid (64 kg) in water (320 L) was added slowly over 2 h. The organic phase was separated and washed with two solutions of NaCl (32 kg) in water (160 L). Silica gel (32 kg) was added to the organic phase and the resulting slurry was stirred for 30 min. The slurry was filtered through a pad of silica gel (160 kg), and the filter "cake" was washed with toluene (296 L). The filtrate was then concentrated to ~50 L. To the residue was added n-heptane (319 L), and the resulting mixture was cooled to 0° C. and stirred for 10 h. The solid was then filtered and dried to afford Int-4 (11.4 kg, 24% over two steps) as an off-white solid. $^1$H-NMR (400 MHz, CDCl$_3$) δ ppm: 6.70 (d, J=83.4 Hz, 1H), 5.80 (s, 2H), 4.63 (t, J=1.2 Hz, 2H), 3.76 (t, J=4.0 Hz, 2H), 2.23 (s, 6H).

Procedure E: Preparation of Tert-Butyl (E)-(3-Fluoro-2-(Hydroxymethyl)Allyl)Carbamate (Int-5)

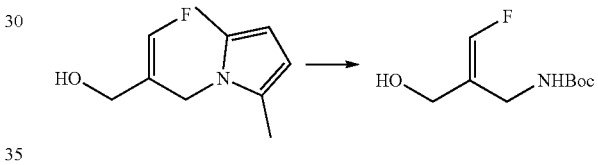

To a reaction vessel charged with Int-4 (2.0 kg), hydroxylamine hydrochloride (3.80 kg) and water (8.00 L) was added a solution of potassium hydroxide (1.20 kg) in water (10.0 L). The resulting mixture was heated to reflux and stirred for 18 h. After cooling to rt, the reaction mixture was filtered and the filter "cake" washed with water (6.0 L). To the filtrate was then added sodium carbonate (3.46 kg) and the resulting mixture was stirred for 30 min. Acetone (9.1 L) was added dropwise at 20° C., and the mixture was stirred for 2 h. Finally, a solution of di-tert-butyldicarbonate (2.37 kg) in MTBE (10 L) was added and stirring was then continued for a further 18 h at 15° C. The organic layer was then separated and washed with aqueous NaOH (1.0 M; 16 L×4). To the organic layer was added silica gel (2.0 kg) and the resulting slurry was stirred for 30 min. The mixture was then filtered and the filter "cake" was washed with MTBE (10 L). The filtrate was concentrated in vacuo to afford Int-5 (2.0 kg, 89%). $^1$H-NMR (400 MHz, CDCl$_3$) δ ppm: 6.78 (d, J=81.2 Hz, 1H), 4.86 (br. s, 1H), 4.00-3.96 (m, 4H), 1.45 (s, 9H).

Procedure F: Preparation of Tert-Butyl (E)-(2-(Bromomethyl)-3-Fluoroallyl)Carbamate (Int-6)

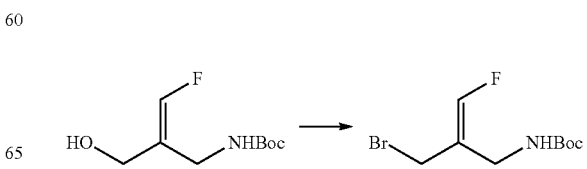

To a vessel charged with Int-5 (4.0 kg), DIPEA (10.2 L) and THF (40.0 L) at 5° C. was added a solution of methanesulfonic anhydride (5.78 kg) in THF (20.0 L). The resulting mixture was stirred for 30 min. To this was added lithium bromide (8.47 kg) and stirring was continued at 5° C. for 2 h. Water (20.0 L) was then added dropwise to the reaction mixture. The organic layer was separated and concentrated to ~8.0 L. To this was added ethyl acetate (24 L) and water (20 L). The organic layer was again separated and concentrated to ~12 L. Heptane (40 L) and silica gel (2.0 kg) was added and the resulting slurry was stirred for 30 min. The slurry was then filtered and the filter "cake" was washed with n-heptane (20 L). The filtrate was concentrated to dryness in vacuo. Further n-heptane was added and stirring was continued at 5° C. for 1 h. The resulting solid was collected by filtration and dried under vacuum at 30° C. to afford Int-6 (3.20 kg, 61%). $^1$H-NMR (400 MHz, CDCl$_3$) δ ppm: 6.78 (d, J=81.2 Hz, 1H), 4.68 (br.s, 1H), 4.00 (d, J=4.4 Hz, 2H), 3.96 (d, J=3.2 Hz, 2H), 1.45 (s, 9H).

Example 2

Preparation of (E)-4-((2-(Aminomethyl)-3-Fluoroallyl)Oxy)Benzonitrile Hydrochloride (Compound 1)

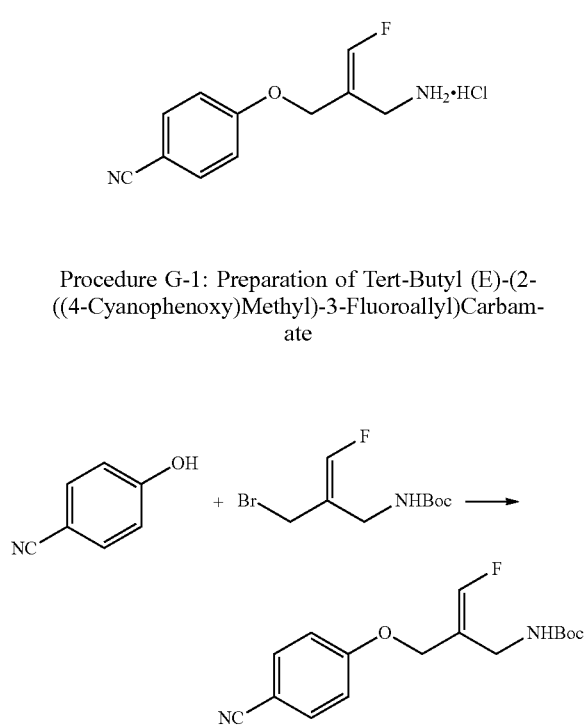

Procedure G-1: Preparation of Tert-Butyl (E)-(2-((4-Cyanophenoxy)Methyl)-3-Fluoroallyl)Carbamate To a stirring solution of 4-hydroxybenzonitrile (1.20 g) in acetonitrile (25.0 mL) at rt was added sequentially potassium carbonate (2.78 g) and Int-6 (2.70 g). The resulting suspension was left to stir at rt overnight. The reaction mixture was filtered through a plug of Celite® to remove the inorganics, and the filtrate was concentrated in vacuo to give a white solid. The solid was then crystalized from diethyl ether/pentane to afford tert-butyl (E)-(2-((4-cyanophenoxy)methyl)-3-fluoroallyl)carbamate (2.81 g, 91%) as a white solid.

Procedure G-2: Alternative Preparation of Tert-Butyl (E)-(2-((4-Cyanophenoxy)Methyl)-3-Fluoroallyl)Carbamate To a stirring solution of 4-hydroxybenzonitrile (2.7 kg) in DMSO (10.15 L) at rt was added sequentially potassium carbonate (4.05 kg) and Int-6 (5.1 kg). The resulting suspension was stirred for 4 hours. Water (50.75 L) was added and the mixture was stirred for 1 hour. The product was filtered and washed with water (10 L). The crude product was dissolved in DMSO (15 L). Water (60 L) was slowly added and the mixture was stirred for 1 hour. The product was filtered, washed with water (10 L) and dried at 55° C. tert-butyl (E)-(2-((4-cyanophenoxy)methyl)-3-fluoroallyl)carbamate (5.1 kg, 89%) was obtained as a white solid.

$^1$H-NMR (300 MHz, CDCl$_3$) δ ppm: 7.65-7.58 (m, 2H), 7.02-6.95 (m, 2H), 6.78 (dp, J=81.6, 1.1 Hz, 1H), 4.52 (dd, J=3.7, 1.2 Hz, 2H), 4.05-3.98 (m, 2H), 1.42 (s, 9H); MS: 207.0 [M-Boc+H]$^+$.

Procedure H-1: Preparation of (E)-4-((2-(Aminomethyl)-3-Fluoroallyl)Oxy)Benzonitrile Hydrochloride (Compound 1)

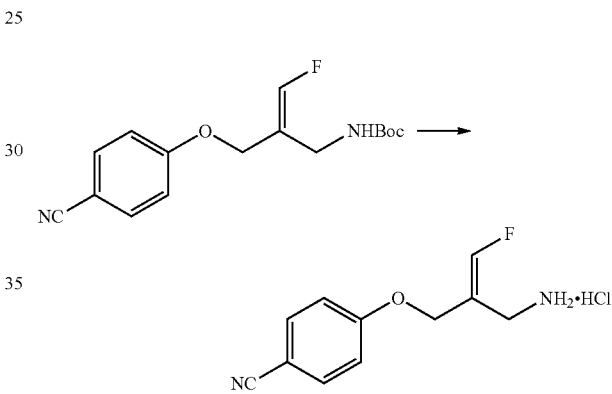

To a stirring solution of tert-butyl (E)-(2-((4-cyanophenoxy)methyl)-3-fluoroallyl)carbamate (2.75 g) in CH$_2$Cl$_2$ (40.0 mL) at rt was added TFA (40.0 mL). The resulting solution was left to stir at rt for 2 h. LC-MS analysis after this time indicated complete consumption of starting material. The reaction mixture was concentrated in vacuo, and residual TFA was removed by co-evaporation with ethyl acetate (20 mL×2) to afford an off-white solid. The solid was dissolved in ethyl acetate (10.0 mL) and HCl (2.0 M in diethyl ether; 40.0 mL) was added resulting in immediate precipitation of a white solid. After stirring for 15 min the solid was collected by filtration and dried under high vacuum to afford crude product (2.11 g). Crude material (1.75 g) was crystalized from hot isopropanol/methanol (17.5 mL/3.50 mL) to afford Compound 1 (1.26 g, 72%) as a white solid.

Procedure H-2: Alternative Preparation of (E)-4-((2-(Aminomethyl)-3-Fluoroallyl)Oxy)Benzonitrile Hydrochloride (Compound 1)

To a stirring solution of tert-butyl (E)-(2-((4-cyanophenoxy)methyl)-3-fluoroallyl)carbamate (5.1 kg) in ethyl acetate (25.5 L) at rt was added 6 M HCl in ethyl acetate (25.5 L). The resulting solution was left to stir at rt for 2 h. LC-MS analysis after this time indicated complete consumption of starting material. The precipitated product was filtered and washed with ethyl acetate (10 L). The crude product was suspended in ethyl acetate (40 L) and the mixture was stirred for 4 hours. The product was filtered and washed with ethyl acetate (10 L) and dried at 60° C. The solid was dissolved in water (16 L) and the mixture was heated to 55° C. The mixture was cooled to 0-5° C. and the solid was filtered. The product was dried at 45° C. under vacuum to afford Compound 1 (3.3 kg, 76%) as a white solid containing ca. 7% moisture.

$^1$H NMR (500 MHz, DMSO-d$_6$) δ ppm: 8.36 (s, 3H), 7.86-7.72 (m, 2H), 7.32 (d, J=81.9 Hz, 1H), 7.19-7.09 (m, 2H), 4.74 (d, J=3.3 Hz, 2H), 3.57 (d, J=2.0 Hz, 2H). MS: 207.0 [M+H]$^+$.

Example 3

Preparation of (E)-4-((2-(Aminomethyl)-3-Fluoroallyl)Oxy)-2-Fluorobenzonitrile Hydrochloride (Compound 2)

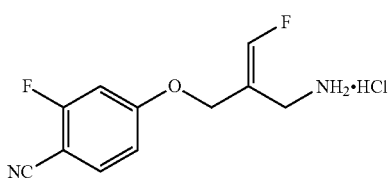

Procedure I: Preparation of Tert-Butyl (E)-(2-((4-Cyano-3-Fluorophenoxy)Methyl)-3-Fluoroallyl) Carbamate

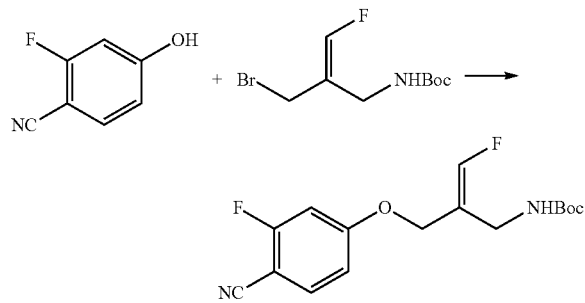

To a stirring solution of 2-fluoro-4-hydroxybenzonitrile (411 mg) and Int-6 (804 mg) in DMF (2.0 mL) was added cesium carbonate (1.17 g). The resulting mixture was stirred for 4 h after which time LC-MS analysis indicated complete consumption of starting materials. Water (20 mL) was then added and the resulting suspension was sonicated and stirred for 10 min. The solid was collected by filtration, washed with water, and then dried at 60° C. for 1 h to afford tert-butyl (E)-(2-((4-cyano-3-fluorophenoxy)methyl)-3-fluoroallyl)carbamate (888 mg, 91%) as a white powder. $^1$H-NMR (300 MHz, CDCl$_3$) δ ppm: 7.55 (dd, J=8.6, 7.5 Hz, 1H), 6.83-6.72 (m, 2H), 6.78 (dp, J=81.0, 1.1 Hz, 1H), 4.51 (dd, J=3.7, 1.2 Hz, 2H), 4.01 (ddd, J=6.3, 2.5, 1.0 Hz, 2H), 1.43 (s, 9H); MS: 325.0 [M+H]$^+$.

Procedure J: Preparation of (E)-4-((2-(Aminomethyl)-3-Fluoroallyl)Oxy)-2-Fluorobenzonitrile Hydrochloride (Compound 2)

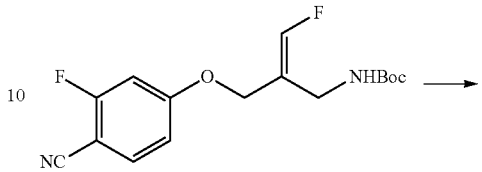

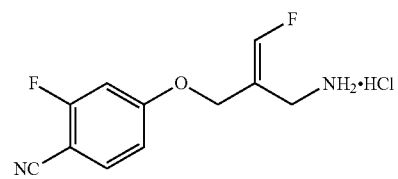

To a stirring solution of tert-butyl (E)-(2-((4-cyano-3-fluorophenoxy)methyl)-3-fluoroallyl)carbamate (50.0 mg) in CH$_2$Cl$_2$ (3.0 mL) was added TFA (0.50 mL). The resulting mixture was stirred for 2 h after which time LC-MS analysis indicated complete consumption of starting material. The reaction mixture was concentrated to dryness and residual TFA was removed under high vacuum. After dissolving the residue in ethyl acetate (3.0 mL), HCl (2.0 M in diethylether; 77 µL) was added. The mixture was stirred at rt for 30 min during which time a solid precipitated. The reaction mixture was transferred to a vial and the solid was spun down in a centrifuge (4000 rpm, 4.0 min). The supernatant was decanted and the solid was washed with the addition of ethyl acetate. After brief sonication, the vial was returned to the centrifuge and the solid spun down. Removal of the supernatant and then drying of the solid "cake" under high vacuum afforded Compound 2 (36 mg, 90%) as a white powder. $^1$H-NMR (300 MHz, DMSO-d$_6$) δ ppm: 8.35 (s, 3H), 7.88 (dd, J=8.8, 7.9 Hz, 1H), 7.36 (d, J=81.0 Hz, 1H), 7.32-7.17 (m, 1H), 7.05 (dd, J=8.8, 2.4 Hz, 1H), 4.78 (dd, J=3.5, 1.1 Hz, 2H), 3.60 (s, 2H); MS: 225.0 [M+H]$^+$.

Example 4

Preparation of (E)-4-((2-(Aminomethyl)-3-Fluoroallyl)Oxy)-2-Bromobenzonitrile Hydrochloride (Compound 3)

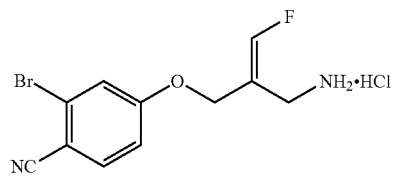

Procedure K: Preparation of Tert-Butyl (E)-(2-((3-Bromo-4-Cyanophenoxy)Methyl)-3-Fluoroallyl) Carbamate

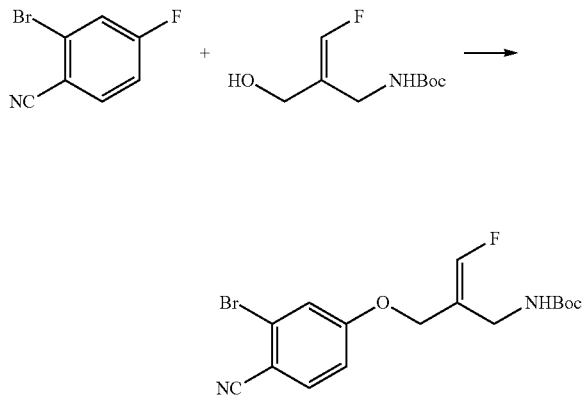

To a stirring solution of Int-5 (573 mg) in DMF (5.0 mL) was added NaH (60% in paraffin oil; 120 mg) at 0° C. and stirred at rt for 30 min. A solution of 2-bromo-4-fluorobenzonitrile (500 mg) in DMF (5.0 mL) was then added dropwise at 0° C. Stirring at rt was continued for 2 h. The reaction mixture was cooled to 0° C. and quenched with saturated aqueous NH$_4$Cl solution. The product was extracted with ethyl acetate (20 mL×3), and the combined organic layers were dried over Na$_2$SO$_4$, and then concentrated in vacuo to give tert-butyl (E)-(2-((3-bromo-4-cyanophenoxy)methyl)-3-fluoroallyl)carbamate (750 mg, 82%). MS: 385.0 [M+H]$^+$.

Procedure L: Preparation of (E)-4-((2-(Aminomethyl)-3-Fluoroallyl)Oxy)-2-Bromobenzonitrile Hydrochloride (Compound 3)

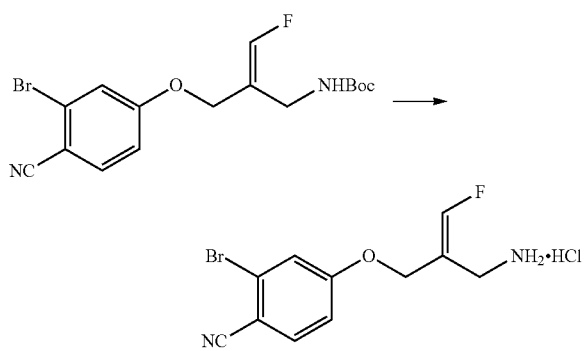

To a stirring solution of tert-butyl (E)-(2-((3-bromo-4-cyanophenoxy)methyl)-3-fluoroallyl)carbamate (100 mg) in 1,4-dioxane (2.0 mL) at 0° C. was added HCl (4.0 M in 1,4-dioxane; 2.0 mL). The resulting mixture was stirred at rt for 3 h. The reaction mixture was concentrated in vacuo and the residue was triturated with ethyl acetate. The resulting solid was isolated and dried to afford Compound 3 (58.6 mg, 79%) as white solid. $^1$H-NMR (Methanol-d$_4$, 400 MHz) δ ppm: 7.76 (d, J=8.0 Hz, 1H), 7.47 (d, J=2.4 Hz, 1H), 7.38-7.16 (m, 2H), 4.72 (d, J=2.8 Hz, 2H), 3.84 (d, J=2.0 Hz, 2H); MS MS: 285.0 [M+H]$^+$.

Example 5

Preparation of (E)-4-((2-(Aminomethyl)-3-Fluoroallyl)Oxy)-3-Fluorobenzonitrile Hydrochloride (Compound 4)

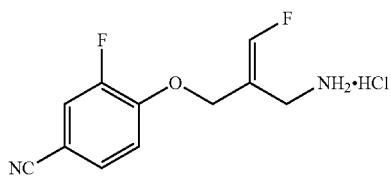

Procedure M: Preparation of Tert-Butyl (E)-(2-((4-Cyano-2-Fluorophenoxy)Methyl)-3-Fluoroallyl) Carbamate

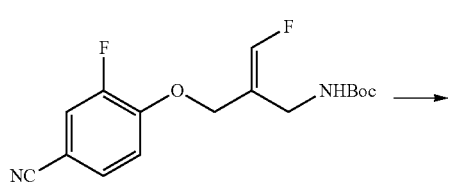

To a stirring solution of 3-fluoro-4-hydroxybenzonitrile (112 mg) in acetonitrile (4.0 mL) at rt was added sequentially potassium carbonate (206 mg) and Int-6 (200 mg). The reaction mixture was filtered through a plug of Celite® to remove the inorganics, and the filtrate was concentrated in vacuo to afford tert-butyl (E)-(2-((4-cyano-2-fluorophenoxy)methyl)-3-fluoroallyl)carbamate (230 mg, 95%) as a white solid. This material was used in the next step without purification. $^1$H-NMR (300 MHz, CDCl$_3$) δ ppm: 7.47-7.37 (m, 2H), 7.06 (t, J=8.3 Hz, 1H), 6.80 (dp, J=81.4, 1.1 Hz, 1H), 4.63-4.57 (m, 2H), 4.03 (ddd, J=6.3, 2.5, 1.0 Hz, 2H), 1.42 (s, 9H); MS: 225.0 [M-Boc+H]$^+$.

Procedure N: Preparation of (E)-4-((2-(Aminomethyl)-3-Fluoroallyl)Oxy)-3-Fluorobenzonitrile Hydrochloride (Compound 4)

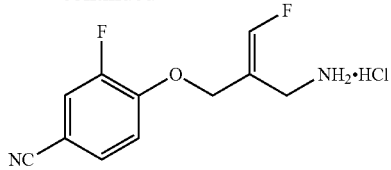

To a stirring solution of tert-butyl (E)-(2-((4-cyano-2-fluorophenoxy)methyl)-3-fluoroallyl)carbamate (230 mg) in CH$_2$Cl$_2$ (10.0 mL) at rt was added TPA (10.0 mL). The resulting solution was left to stir at rt for 2 h. LC-MS analysis after this time indicated complete consumption of starting material. The reaction mixture was concentrated in vacuo, and residual TFA was removed by co-evaporation with ethyl acetate (20 mL×2) to afford an off-white solid. The solid was dissolved in ethyl acetate (10.0 mL) and HCl (2.0 M in diethyl ether; 5.00 mL) was added resulting in immediate precipitation of a white solid. After stirring for 15 min the contents of the reaction vessel were transferred to a vial. The solid was then spun down in a centrifuge (4000 rpm, 2 min, 20° C.). The supernatant was carefully decanted and the solid "cake" was washed with further ethyl acetate. The solid was once again spun down and the supernatant decanted. The solid "cake" was dried under high vacuum to afford Compound 4 (181 mg, 98%). $^1$H-NMR (Methanol-d$_4$, 300 MHz) δ ppm: 7.65-7.56 (m, 2H), 7.36 (t, J=8.6 Hz, 1H), 7.30 (dt, J=81.2, 0.9 Hz, 1H), 4.80 (dd, J=3.5, 1.1 Hz, 2H), 3.90-3.82 (m, 2H); MS: 225.0 [M+H]$^+$.

Example 6

Preparation of (E)-4-((2-(Aminomethyl)-3-Fluoroallyl)Oxy)-2-Methylbenzonitrile Hydrochloride (Compound 5)

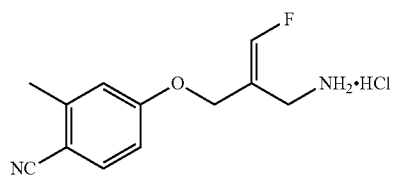

Procedure O: Preparation of Tert-Butyl (E)-(2-((4-Cyano-3-Methylphenoxy)Methyl)-3-Fluoroallyl) Carbamate

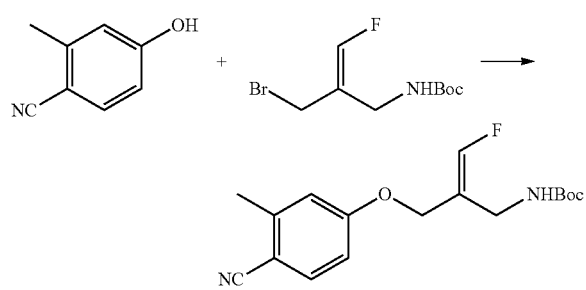

A mixture of 4-hydroxy-2-methylbenzonitrile (109 mg), Int-6 (200 mg) and potassium carbonate (206 mg) in acetonitrile (4.0 mL) was stirred at rt overnight. LCMS analysis after this time showed complete conversion. The reaction mixture was diluted with CH$_2$Cl$_2$ (20 mL), filtered and then concentrated in vacuo to afford tert-butyl (E)-(2-((4-cyano-3-methylphenoxy)methyl)-3-fluoroallyl)carbamate (240 mg, 100%) as an off-white solid. This material was progressed to the next step without further purification. $^1$H-NMR (300 MHz, CDCl$_3$) δ ppm: 7.50 (d, J=8.5 Hz, 1H), 6.84-6.73 (m, 2H), 6.75 (dt, J=81.4, 1.1 Hz, 1H), 4.50-4.43 (m, 2H), 4.01-3.93 (m, 2H), 1.99 (s, 3H), 1.39 (s, 9H); MS: 321.0 [M+H]$^+$.

Procedure P: Preparation of (E)-4-((2-(Aminomethyl)-3-Fluoroallyl)Oxy)-2-Methylbenzonitrile Hydrochloride (Compound 5)

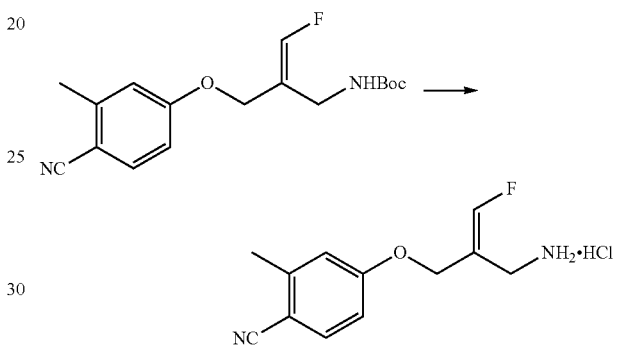

To a stirring solution of tert-butyl (E)-(2-((4-cyano-3-methylphenoxy)methyl)-3-fluoroallyl)carbamate (240 mg) in CH$_2$Cl$_2$ (10 mL) at rt was added TFA (10.0 mL). The resulting solution was left to stir at rt for 2 h. LC-MS analysis after this time indicated complete consumption of starting material. The reaction mixture was concentrated in vacuo, and residual TFA was removed by co-evaporation with CH$_2$Cl$_2$ (20 mL×2) to afford a light yellow oil. The solid was dissolved in ethyl acetate (10.0 mL) and HCl (2.0 M in diethyl ether; 1.00 mL) was added resulting in immediate precipitation of a white solid. After stirring for 15 min the solid was filtered and dried under high vacuum to afford Compound 5 (175 mg, 91%) as a white solid. $^1$H-NMR (Methanol-d$_4$, 300 MHz) δ ppm: 7.63 (d, J=8.6 Hz, 1H), 7.27 (dt, J=81.0, 0.9 Hz, 1H), 7.08-7.04 (m, 1H), 6.99 (ddd, J=8.6, 2.6, 0.6 Hz, 1H), 4.70 (dd, J=3.6, 1.1 Hz, 2H), 3.84 (d, J=2.1 Hz, 2H), 2.53 (d, J=0.7 Hz, 3H); MS: 221.0 [M+H]$^+$.

Comparative Example 7

Preparation of (−)-(E)-2-(2,3-Dihydrobenzofuran-2-Yl)-3-Fluoroprop-2-En-1-Amine Hydrochloride (PXS-5131)

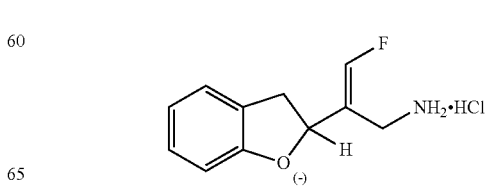

Procedure Q: Preparation of 2,3-Dihydrobenzofuran-2-Carbonyl Chloride

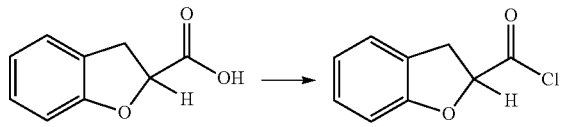 [SMILES: O=C(O)C1Cc2ccccc2O1 ; O=C(Cl)C1Cc2ccccc2O1]

To a stirring solution of 2,3-dihydrobenzofuran-2-carboxylic acid (78.0 g) and DMF (1.0 mL) in CH$_2$Cl$_2$ (780 mL) at 0° C. was added oxalyl chloride (125 mL) dropwise. The reaction progress was monitored by TLC. After complete consumption of the starting material, the reaction mixture was concentrated in vacuo to afford 2,3 dihydrobenzofuran-2-carbonyl chloride (92.0 g) as a crude, red oil. This material was not characterized and used immediately in the following step.

Procedure R: Preparation of 2-Diazo-1-(2,3-Dihydrobenzofuran-2-Yl)Ethanone

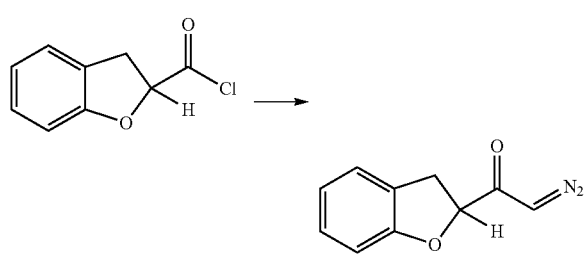

To a cold (0° C.), stirring solution of (trimethylsilyl) diazomethane (2 M in diethyl ether; 546 mL) in THF/CH$_3$CN (1:1; 780 mL) under N$_2$ was added a solution of crude 2,3-dihydrobenzofuran-2-carbonyl chloride in THF/CH$_3$CN (1:1; 780 mL) dropwise. The resulting mixture was left to stir at 0° C. for 1 h. The reaction mixture was then evaporated in vacuo to give 2-diazo-1-(2,3-dihydrobenzofuran-2-yl)ethanone (92.6 g) as a crude, brown oil. This material was used immediately in the subsequent step, without purification. $^1$H-NMR (400 MHz; CDCl$_3$) δ ppm: 3.24 (dd, J=16.4, 5.6 Hz, 1H), 3.39 (dd, J=16.4, 10.4 Hz, 1H), 4.95 (dd, J=10.8, 5.6 Hz, 1H), 5.67 (s, 1H), 6.70 (d, J=8.0 Hz, 1H), 6.75 (dd, J=6.9, 6.8 Hz, 1H), 6.98-7.04 (m, 2H).

Procedure S: Preparation of 2-Bromo-1-(2,3-Dihydrobenzofuran-2-Yl)Ethanone

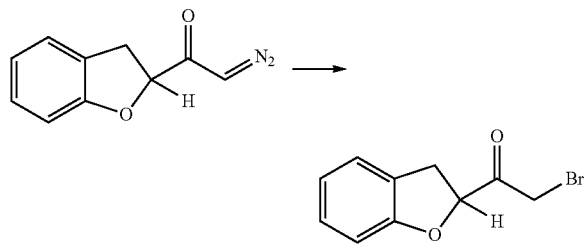

To a stirring solution of crude 2-diazo-1-(2,3-dihydrobenzofuran-2-yl)ethanone (92.6 g) in CH$_2$Cl$_2$ (926 mL) at 0° C. was added HBr/AcOH (48%, 216 mL) dropwise. The resulting mixture was left to stir at this temperature for 15 min. The reaction mixture was diluted with water (800 mL) and the aqueous layer was extracted with CH$_2$Cl$_2$ (300 mL). The combined organics were washed with saturated aqueous NaHCO$_3$ (600 mL×3) and then brine (800 mL). After drying over Na$_2$SO$_4$, the solvent was removed in vacuo to afford 2-bromo-1-(2,3-dihydrobenzofuran-2-yl)ethanone (98.0 g) as a crude brown oil. This material was immediately progressed to the subsequent step, without purification. $^1$H-NMR (400 MHz; CDCl$_3$) δ ppm: 3.41 (dd, J=16.0, 6.4 Hz, 1H), 3.59 (dd, J=16.0, 10.8H, 1 Hz), 4.18 (d, J=14.4 Hz, 1H), 4.35 (d, J=14.0 Hz, 1H), 5.30 (dd, J=12.4, 6.4 Hz, 1H), 6.88 (d, J=8.0 Hz, 1H), 6.92 (dd, J=7.4, 7.4 Hz, 1H), 7.15-7.20 (m, 2H).

Procedure T: Preparation of 2-Azido-1-(2,3-Dihydrobenzofuran-2-Yl)Ethanone

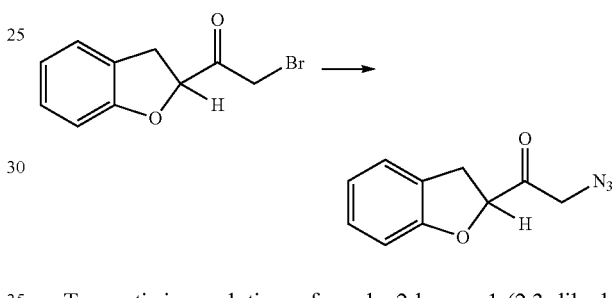

To a stirring solution of crude 2-bromo-1-(2,3-dihydrobenzofuran-2-yl)ethanone (98.0 g) in acetone (926 mL) at 0° C. was added NaN$_3$ (132 g). The resulting mixture was left to stir at this temperature for 3 h. The reaction mixture was partitioned between water (1 L) and ethyl acetate (800 mL), and the aqueous layer was extracted with further ethyl acetate (800 mL×2). The combined organics were washed with brine (1 L), dried over Na$_2$SO$_4$, and then concentrated in vacuo to give 2-azido-1-(2,3-dihydrobenzofuran-2-yl) ethanone (92 g) as a crude, brown oil. This material was progressed to the subsequent step, without purification. $^1$H-NMR (400 MHz; CDCl$_3$) δ ppm: 3.44 (dd, J=16.4, 6.0 Hz, 1H), 3.54 (dd, J=16.0, 11.2 Hz, 1H), 4.19 (d, J=19.2 Hz, 1H), 4.38 (d, J=19.2 Hz, 1H), 5.17 (dd, J=11.2, 6.0 Hz, 1H), 6.88 (d, J=8.0 Hz, 1H), 6.93 (dd, J=8.0, 7.9 Hz, 1H), 7.15-7.26 (m, 2H).

Procedure U: Preparation of Tert-Butyl 2-(2,3-Dihydrobenzofuran-2-Yl)-2-Oxoethylcarbamate

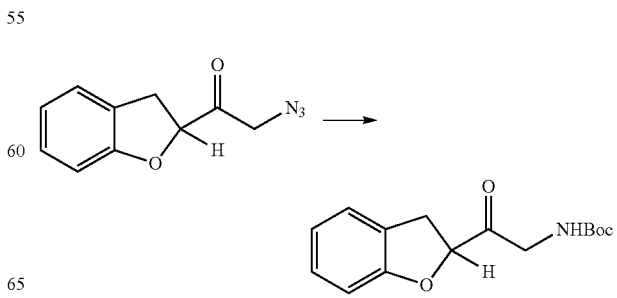

A solution of crude azido-1-(2,3-dihydrobenzofuran-2-yl) ethanone (91.0 g) in ethyl acetate (910 mL) was charged with di-tert-butyl dicarbonate (135 g) and Pd/C (10%; 9.10 g, 50% wet). The resulting suspension was stirred at rt under an atmosphere of $H_2$ overnight. The catalyst was removed by filtration, and the filtrate was evaporated in vacuo. The crude material was purified over silica gel, eluting with petroleum ether/ethyl acetate (20:1) to afford tert-butyl 2-(2,3-dihydrobenzofuran-2-yl)-2-oxoethylcarbamate (39.0 g, 33%) as a yellow solid. $^1$H-NMR (400 MHz; CDCl$_3$) δ ppm: 1.43 (s, 9H), 3.36 (dd, J=16.0, 6.4 Hz, 1H), 3.53 (dd, J=16.0, 10.8 Hz, 1H), 4.22 (dd, J=21.2, 4.8 Hz, 1H), 4.41 (dd, J=20.4, 4.8 Hz, 1H), 5.16 (dd, J=11.2, 6.4 Hz, 1H), 6.87 (d, J=8.0 Hz, 1H), 6.90 (dd, J=7.6, 7.2 Hz, 1H), 7.14-7.18 (m, 2H).

Procedure V: Preparation of (E)-Tert-Butyl 2-(2,3-Dihydrobenzofuran-2-Yl)-3-Fluoroallylcarbamate and (Z)-Tert-Butyl 2-(2,3-Dihydrobenzofuran-2-Yl)-3-Fluoroallylcarbamate

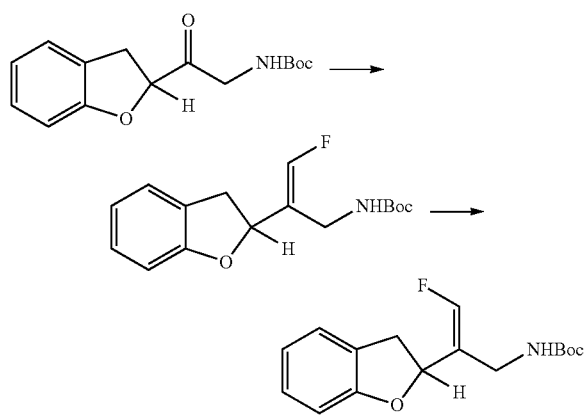

To a stirring solution of fluoromethyl(triphenyphosphonium)tetrafluoroborate (75.6 g) in THF (910 mL) at −25° C. under Na was slowly added NaHMDS (1.0 M in THF; 246 mL). The mixture was left to stir at −25° C. for 30 min, then cooled to −78° C. To the reaction mixture was then added a solution of tert-butyl 2 (2,3 dihydrobenzofuran-2-yl)-2-oxoethylcarbamate (45.6 g) in THF (364 mL). After complete addition, stirring was continued at −78° C. for 1 h. The reaction mixture was partitioned between water (1.2 L) and ethyl acetate (1.2 L), and the aqueous layer was extracted with further ethyl acetate (800 mL×2). The combined organics were washed with brine (1.5 L), dried over Na$_2$SO$_4$, and then concentrated in vacuo. Initial purification of the crude material was performed over silica gel, eluting with petroleum ether/ethyl acetate (30:1 to 10:1) to afford a mixture of rac. (E)-tert-butyl 2-(2,3-dihydrobenzofuran-2-yl)-3-fluoroallylcarbamate and rac. (Z)-tert-butyl dihydrobenzofuran-2-yl)-3-fluoroallylcarbamate (1:1; 9.70 g). The mixture was then subjected to preparative HPLC purification to give (E)-tert-butyl 2-(2,3-dihydrobenzofuran-2-yl)-3-fluoroallylcarbamate (4.10 g, 9%) and (Z)-tert-butyl 2-(2,3-dihydrobenzofuran-2-yl)-3-fluoroallylcarbamate (3.60 g, 8%). (E)-tert-butyl 2-(2,3-dihydrobenzofuran-2-yl)-3-fluoroallylcarbamate: $^1$H NMR (300 MHz; CDCl$_3$) δ ppm: 1.42 (s, 9H), 3.18 (dd, J=15.7, 8.5 Hz, 1H), 3.39 (dd, J=15.7, 9.4 Hz, 1H), 3.93 (dd, J=14.3, 3.1 Hz, 1H), 4.05 (dd, J=14.9, 5.3 Hz, 1H), 4.75 (br. s, 1H), 5.23 (dd, J=9.4, 9.4 Hz, 1H), 6.79 (d, J=82.7 Hz, 1H), 6.80 (d, J=8.0 Hz, 1H) 6.88 (ddd, J=7.5, 7.5, 1.0 Hz, 1H), 7.14 (dd, J=8.0, 7.9 Hz, 1H), 7.18 (d, J=7.5 Hz, 1H).

Procedure W: Separation of the Two Enantiomers of Racemic (E)-Tert-Butyl Dihydrobenzofuran-2-Yl)-3-Fluoroallylcarbamate

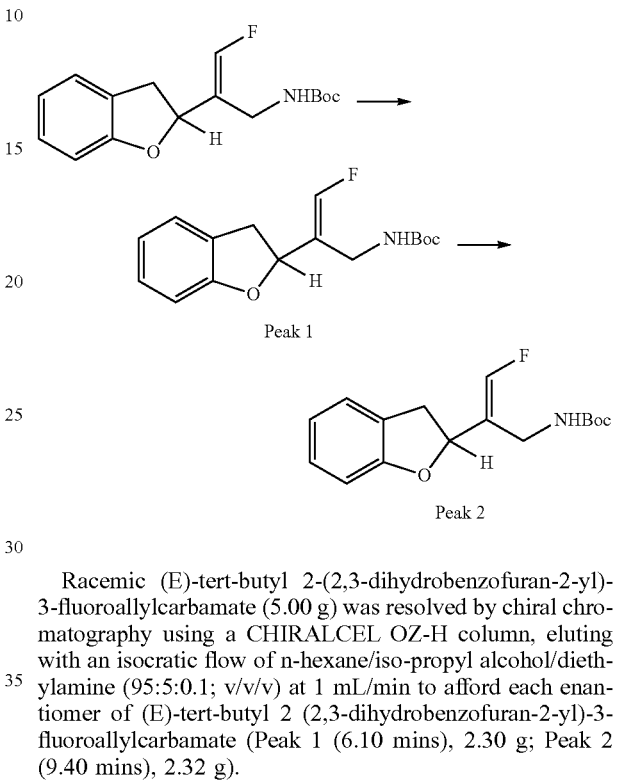

Racemic (E)-tert-butyl 2-(2,3-dihydrobenzofuran-2-yl)-3-fluoroallylcarbamate (5.00 g) was resolved by chiral chromatography using a CHIRALCEL OZ-H column, eluting with an isocratic flow of n-hexane/iso-propyl alcohol/diethylamine (95:5:0.1; v/v/v) at 1 mL/min to afford each enantiomer of (E)-tert-butyl 2 (2,3-dihydrobenzofuran-2-yl)-3-fluoroallylcarbamate (Peak 1 (6.10 mins), 2.30 g; Peak 2 (9.40 mins), 2.32 g).

Procedure X: Preparation of (−)-(E)-2-(2,3-Dihydrobenzofuran-2-Yl)-3-Fluoroprop-2-En-1-Amine Hydrochloride (PXS-5131)

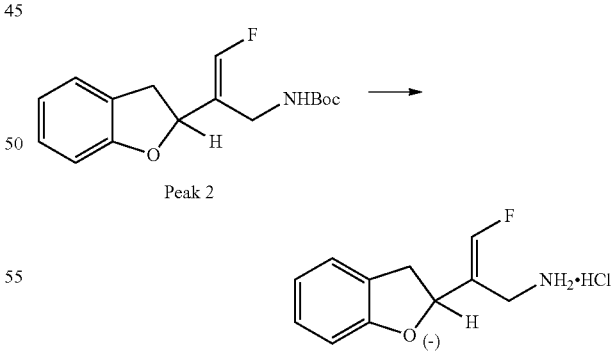

To a stirring solution of the enantiomer represented by Peak 2 of purified (E)-tert-butyl 2-(2,3-dihydrobenzofuran-2-yl)-3-fluoroallylcarbamate (30 mg) in methanol (1.0 mL) at rt was added HCl (2.0 M in diethyl ether; 1.0 mL). The resulting mixture was left to stir at rt for 2 h. All volatiles were removed in vacuo, and the resulting residue was taken up in ethyl acetate (0.5 mL). After addition of diethyl ether (2.0 mL), a white precipitate resulted. The contents were transferred to a vial, and spun down in a centrifuge (4000 rpm, 4 min.) to give a solid "cake". After decanting the supernatant, more diethyl ether was added, and (after brief sonication) the vial was returned to the centrifuge. This process of centrifugation/washing was repeated a total of three times. The solid, thus obtained, was dried under high vacuum to afford PXS-5131 (13 mg, 62%). $[\alpha]_D$=−26.02°, c=11.2 mg/mL in methanol; $^1$H-NMR (300 MHz; Methanol-$d_4$) δ ppm: 3.19 (dd, J=15.9, 9.1 Hz, 1H), 3.41 (dd, J 15.9, 9.2 Hz, 1H), 3.72 (dd, J=14.0, 2.6 Hz, 1H), 3.84 (ddd, J=13.6, 2.1, 0.5 Hz, 1H), 5.36 (dd, J=9.1, 9.1 Hz, 1H), 6.83 (d, J=8.0 Hz, 1H), 6.90 (ddd, J=7.5, 7.5, 0.9 Hz, 1H), 7.15 (dd, J=7.6, 7.6 Hz, 1H), 7.22 (d, J=80.9 Hz, 1H), 7.24 (d, J=7.4 Hz, 1H); MS: 194.0 [M+H]$^+$. [Note: Deprotection of Peak 1 from procedure W afforded a compound with an $[\alpha]_D$ of similar magnitude but of opposite sign]

Comparative Example 8

The following compounds outlined in TABLE 2 have been included for the purpose of comparison only. These compounds can be synthesized using analogous methods to those described herein, with the exception of Compound 6 and Compound 14.

These compounds can be prepared according to the procedures described in Foot J. S., et al., *J. Pharm. Exp. Ther.*, 2013, 347, 365-374, from commercially available 4-hydroxybenzonitrile.

TABLE 2

| Compound | Structure | m/z [M + H]$^+$ |
|---|---|---|
| 6 | (4-cyanophenoxy derivative) | 207.0 |
| 7 | (3-methoxy-4-cyanophenoxy derivative) | 237.0 |
| 8 | (2-cyanophenoxy derivative) | 207.0 |
| 9 | (3-cyanophenoxy derivative) | 207.0 |
| 10 | (phenoxy derivative) | 182.0 |
| 11 | (4-trifluoromethylphenoxy derivative) | 250.0 |
| 12 | (4-methylsulfonylphenoxy derivative) | 260.0 |
| 13 | (4-trifluoromethoxyphenoxy derivative) | 266.0 |
| 14 | (4-methoxyphenoxy derivative) | 212.0 |

Example 9

Method to Determine the Ability of Compounds of Formula I to Inhibit Human Recombinant SSAO/VAP-1

Human recombinant SSAO/VAP-1 amine oxidase activity was determined using the method as described for monoamine oxidase, copper-containing amine oxidases and related enzymes (Holt A. and Palcic M., *Nat. Protoc.* 2006, 1, 2498-2505). Briefly, a cloned cDNA template corresponding to residues 34-763 of human SSAO/VAP-1, and incorporating a mouse Ig kappa (κ) signal sequence, N-terminal flag epitope tag and tobacco etch virus (TEV) cleavage site, was assembled in a mammalian expression vector (pLO-CMV) by Geneart AG. This vector containing human SSAO/VAP-1 residues was transfected into CHO-K1 glycosylation mutant cell line, Lec 8. A clone stably expressing human SSAO/VAP-1 was isolated and cultured in large scale. Active human SSAO/VAP-1 was purified and recovered using immunoaffinity chromatography. This was used as the source for SSAO/VAP-1 activity. A high-throughput colorimetric assay was developed using either 96 or 384 well format. Briefly, in a standard 96 well plate assay 50 μL of purified human SSAO/VAP-1 (0.25 μg/mL) in 0.1 M sodium phosphate buffer (pH 7.4) was added into each well. Test compounds were dissolved in DMSO and tested in a Concentration Response Curve (CRC) with 4-11 data points, typically in the micromolar or nanomolar range after incubation with human SSAO/VAP-1 for 30 min at 37° C. After 30 min incubation, 50 μL of the reaction mixture containing 600 µM benzylamine (Sigma Aldrich), 120 µM Amplex Red (Sigma Aldrich) and 1.5 U/mL horseradish peroxidase (Sigma Aldrich) prepared in 0.1 M sodium phosphate buffer (pH 7.4) were added to the corresponding well. The fluorescence unit (RFU) was read every 2.5 min for 30 min at 37° C. excitation 565 nm and emission 590 nm (Optima; BMG labtech). The slope of the kinetics for each well was calculated using MARS data analysis software (BMG labtech) and this value was used to deduce the $IC_{50}$ value (Dotmatics). The ability of the compounds of Formula I to inhibit SSAO/VAP-1 is shown in Table 3.

Example 10

Method to Determine the Ability of Compounds of Formula I to Inhibit Human Recombinant MAO-B The ability of the compounds of this invention to inhibit MAO-B activities in vitro was tested. Recombinant human MAO-B (0.06 mg/mL; Sigma Aldrich) was used as source of MAO-B enzyme activities. The assay was performed in a similar way as for human SSAO/VAP-1 (EXAMPLE 9) except, the substrate benzylamine was used at 100 µM and the assay was run after an incubation time of 2 hours. The ability of compounds of Formula I to inhibit MAO-B is shown in Table 3.

Example 11

Method to Determine the Ability of Compounds of Formula I to Inhibit Human Recombinant MAO-A The selectivity of the compounds of this invention was tested by determining their ability to inhibit MAO-A activity in vitro, using recombinant human MAO-A (0.003 mg/mL; Sigma Aldrich). The assay was performed in a similar way as for human SSAO/VAP-1 (EXAMPLE 9) except, the substrate tyramine was used at 100 µM in place of benzylamine and the assay was run after an incubation time of 2 hours. The ability of compounds of Formula I to inhibit MAO-A is shown in Table 3.

TABLE 3*

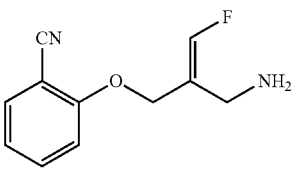 [SMILES: N#Cc1ccccc1OC/C(=C/F)CN]

| Compound | R1 | R2 | X | Y | SSAO $IC_{50}$ 30 min | MAO-B $IC_{50}$ 2 hour | MAO-A $IC_{50}$ 2 hour |
|---|---|---|---|---|---|---|---|
| 1 | H | H | H | F | A1 | A2 | A3 |
| 2 | F | H | H | F | A1 | A2 | A3 |
| 3 | Br | H | H | F | A1 | A2 | B3 |
| 4 | H | F | H | F | A1 | A2 | B3 |
| 5 | Me | H | H | F | A1 | A2 | B3 |
| 6 | H | H | F | H | A1 | A2 | C3 |
| 7 | MeO | H | H | F | B1 | B2 | A3 |
| 8 | 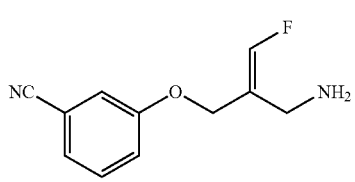 | | | | D1 | A2 | D3 |
| 9 | 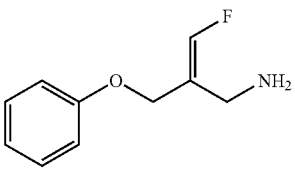 | | | | A1 | A2 | C3 |
| 10 |  | | | | B1 | A2 | C3 |

TABLE 3*-continued

[Structure: R1, R2-substituted phenyl with O-CH2-C(=CXY)-CH2NH2, with NC (cyano) on the ring]

| Compound | R1 | R2 | X | Y | SSAO IC$_{50}$ 30 min | MAO-B IC$_{50}$ 2 hour | MAO-A IC$_{50}$ 2 hour |
|---|---|---|---|---|---|---|---|
| 11 | \multicolumn{4}{l|}{4-CF3-phenyl-O-CH2-C(=CHF)-CH2NH2} | A1 | A2 | B3 |
| 12 | \multicolumn{4}{l|}{4-MeO2S-phenyl-O-CH2-C(=CHF)-CH2NH2} | A1 | D2 | A3 |
| 13 | \multicolumn{4}{l|}{4-F3CO-phenyl-O-CH2-C(=CHF)-CH2NH2} | A1 | A2 | D3 |
| 14 | \multicolumn{4}{l|}{4-MeO-phenyl-O-CH2-C(=CHF)-CH2NH2} | A1 | A2 | C3 |
| PXS-5131 | | | | | A1 | A2 | C3 |

A1 = <10 nM
B1 = 10-500 nM
C1 = >500-1000 nM
D1 = >1000 nM
A2 = <50 nM
B2 = 50-500 nM
C2 = >500-1000 nM
D2 = >1000 nM
A3 = >30000 nM
B3 = >3000 nM-30000 nM
C3 = 300-3000 nM
D3 = <300 nM

*For the purposes of this invention, a potent inhibitor of SSAO/VAP-1 has an IC$_{50}$ of <10 nM (A1) and a potent inhibitor of MAO-B has an IC$_{50}$ <50 nM (A2), under the assay conditions described in EXAMPLES 9 and 10. To be considered selective over MAO-A, the IC$_{50}$ must be >3000 nM (A3 and B3), under the assay conditions described in EXAMPLE 11.

As shown in Table 3, compounds of the invention are potent inhibitors of both human recombinant SSAO/VAP-1 and MAO-B in vitro under the described assay conditions. Importantly, the compounds of the invention are not active against recombinant human MAO-A, an important off-target. Surprisingly, this profile is highly dependent on the nature and the position of the substituents on the phenyl ring.

Example 12

Pharmacokinetic Parameters of Compound 1 and PXS-5131

Pharmacokinetic (PK) studies were carried out at Sundia MediTech Co. Ltd., Shanghai. Wistar rats weighing approximately 280 g were administered either Compound 1 or PXS-5131 by oral gavage at 3 mg/kg. At various times between 15 minutes and 8 hours, blood samples were collected by tail vein bleed. Plasma was analyzed by high performance liquid chromatography-tandem mass spectrometry using a Shimadzu LC30AD HPLC and a QTRAP 5500 mass spectrometer. The time course and basic PK parameters thus obtained are outlined in FIG. 1.

Example 13

Method to Determine the Ability of Compounds of Formula I to Inhibit Rat Adipose Tissue SSAO/VAP-1 and Rat Brain Tissue MAO-B Sprague Dawley rats were orally administered the compound under study and sacrificed at various time points and gonadal fat and brain tissue collected.

Adipose tissue was homogenized in ice-cold HES buffer (20 mM HEPES, 1 mM EDTA, sucrose 250 mM, proteases and phosphatases inhibitor, pH 7.4). Homogenate was then centrifuged at 2000 rpm for 5 minutes at 4° C. and the resultant supernatant portion (minus the lipid top layer) used for assay. SSAO/VAP-1 activity was determined by using a non-specific MAO inhibitor (e.g. pargyline) to establish the high signal and a mixture of non-specific MAO inhibitor and an SSAO/VAP-1 inhibitor (e.g. semicarbazide) to determine the low signal.

Brain tissue was homogenized in ice-cold Tris buffer (10 mM Tris·HCl, 0.5 mM EDTA, sucrose 250 mM, pH 7.4). Homogenate was then centrifuged at 4,000 rpm for 3 minutes at 4° C. The resultant supernatant was transferred and centrifuged again at 4,000 rpm for 3 minutes at 4° C. Process repeated one last time, this time at 10,000 rpm for 8 minutes. Supernatant discarded and the resultant pellet containing the mitochondrial extract re-suspended in 0.1 M sodium phosphate buffer solution (1:3 ratio). MAO-B activity was determined by using a specific MAO-A inhibitor (e.g. clorgyline) and a SSAO/VAP-1 inhibitor (e.g. semicarbazide) to establish the high signal. Low signal was established as for the adipose tissue assay.

Activity of the treated samples was analyzed using the fluorometric method described in EXAMPLE 9 for SSAO/VAP-1 activity and EXAMPLE 10 for MAO-B.

Example 14

Description of Dual Inhibitor PXS-5131

Figure 2:
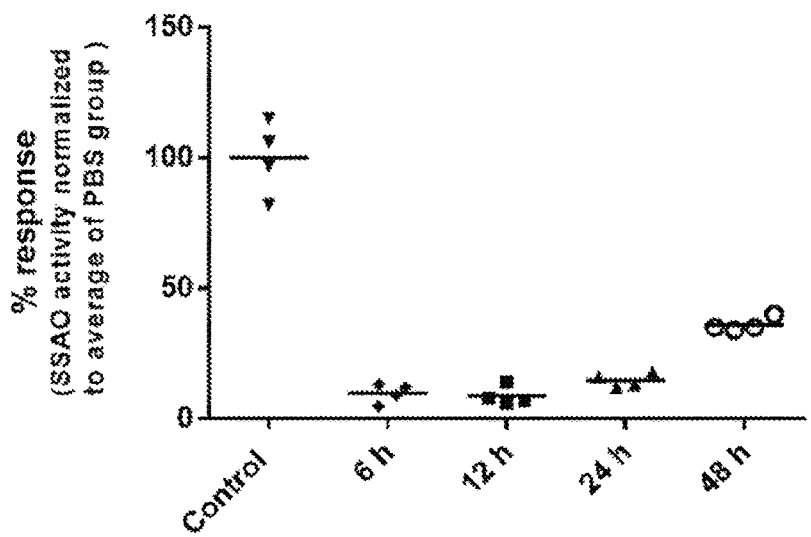
FIG. 2 depicts the pharmacodynamic readout of SSAO/VAP-1 inhibition in vivo in Sprague Dawley rat adipose tissue, after oral administration of PXS-5131 at 0.6 mg/kg.
Figure 3:
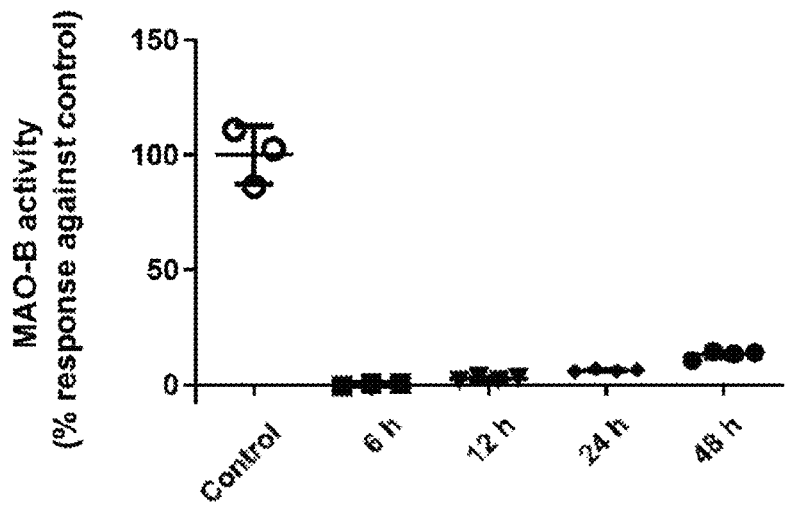
FIG. 3 depicts the pharmacodynamic readout of MAO-B inhibition in vivo in Sprague Dawley rat brain tissue, after oral administration of PXS-5131 at 0.6 mg/kg.

PXS-5131 is a prototype dual inhibitor of both MAO-B and SSAO/VAP-1. The compound possesses a pharmacokinetic profile inferior to Compound 1. Oral administration of a single dose of compound PXS-5131 to Sprague Dawley rats affects long lasting inhibition of SSAO/VAP-1 and MAO-B in vivo, as demonstrated by FIGS. 2 and 3. As depicted in FIG. 2, a single dose of PXS-5131 inhibits SSAO/VAP-1 enzyme activity for greater than 24 hours. As depicted in FIG. 3 a single dose of PXS-5131 inhibits MAO-B enzyme activity for greater than 24 hours. PXS-5131 was used to assess these combined effects in the following in vivo models.

Example 15

Efficacy of Dual Inhibitor PXS-5131 in the Carrageenan Air Pouch Model.

On day 0, BALB/c mice were shaved at the nape of the neck, anesthetized and 6 mL air sterile (0.2 μm, Sartorius, Cat. 16532) was injected subcutaneously using a 23G×1½ inch needle fixed to a 6 mL syringe. The injection site was sealed with flexible collodion (Macron, Cat. 4580-02). On day 3 a further 3 mL of sterile air was injected into the neck.

3% λ-carrageenan was prepared by dissolving 1.8 g λ-carrageenan (FLUKA, Cat. 22049, lot 1408463) in 60 mL hot de-ionized water. Once dissolved, the solution was cooled to room temperature and the volume made up to 60 mL with de-ionized water.

On day six, PXS-5131 in PBS (vehicle) or PBS only were administered by oral gavage to the mice. One hour after administration, mice were injected with 1 mL 3% λ-carrageenan, using a 23G×2 inch needle fitted to a 1 mL syringe, directly into the air pouch. Sham animals were administered 1 mL de-ionized water instead of λ-carrageenan solution.

Four hours after carrageenan/de-ionized water injection, the mice were anesthetized and 3 mL 10 U/mL heparinized saline was injected into the air pouch. The air pouch was gently massaged, the contents immediately removed using an 18G×1 inch needle fitted to a 5 mL syringe, and the exudate volume recorded. An aliquot of the exudate taken for total white blood cell counting; a second aliquot of the exudate was taken for differential white blood cell counts.

Figure 4:
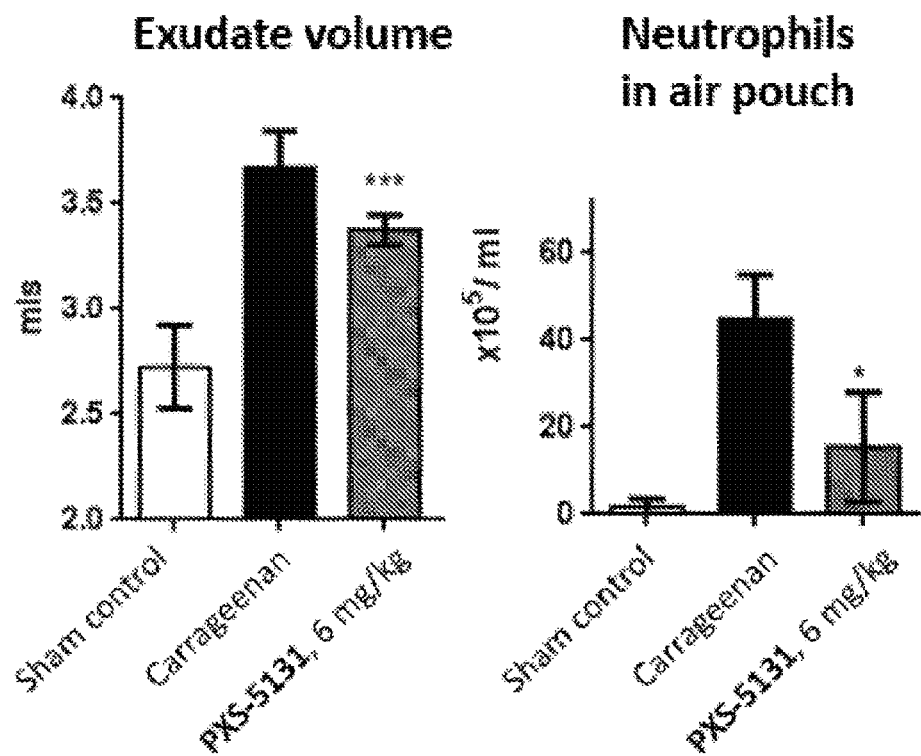
FIG. 4 depicts the anti-inflammatory effects of PXS-5131 in BALB/c mice in the carrageenan air pouch model.

The anti-inflammatory effects of PXS-5131 are shown in FIG. 4. Carrageenan injection caused an increase in inflammation, which was reduced by a single application of PXS-5131, as seen by a decrease in both exudate volume and neutrophil count in the air pouch. *$p<0.05$, $p<0.01$, *$p<0.001$ compared to carrageenan-treated mice (Black bars).

Compound 1 has also been profiled in this model.

Example 16

Efficacy of Dual Inhibitor PXS-5131 in Intranigral Lipopolysaccharide (LPS)-Induced Neuroinflammatory Models Hooded Wistar male rats weighing between 300-400 g were obtained from Adelaide Laboratory Animal Services. On day 0, animals received 2 mg/kg of PXS-5131, or sterile saline (vehicle) via intraperitoneal injection (i.p.) both 1 hour before and 5 hours after LPS infusions.

Dopaminergic Neuron Counts after Unilateral Infusion of LPS

Unilateral infusions: Rats receiving a unilateral injection of 2 μL of 1.5 mg/mL solution of LPS (O55:B5, Sigma) in the substantia nigra were anaesthetized with isofluorane and positioned in a stereotaxic frame. For all rats, holes were drilled into the skull above the appropriate targeted structures according to the following coordinates: −5.3 mm posterior; ±2.0 mm lateral; −8.0 mm ventral to bregma. All rats received a unilateral injection of LPS, leaving the other hemisphere intact Animals received either PXS-5131 (2 mg/kg) or vehicle i.p. daily for two weeks.

Immunohistochemical procedures: two weeks after the lesion, the rats were transcardially perfused with PBS followed by PFA 4%. Brains were post-fixed in PFA 4%, and coronal sections of 30 µm containing the substantia nigra were collected and washed 3×0.01 M phosphate-buffered saline at pH 7.4. (PBS) for 10 minutes. Dopaminergic neurons were stained with anti-tyrosine hydroxylase (TH) antibody 1:10000 and visualized using nickel-enhanced 3,3'-diaminobenzidine (DAB) and counted manually. Values across sections were averaged for each animal and are shown in FIG. 5.

Figure 5:
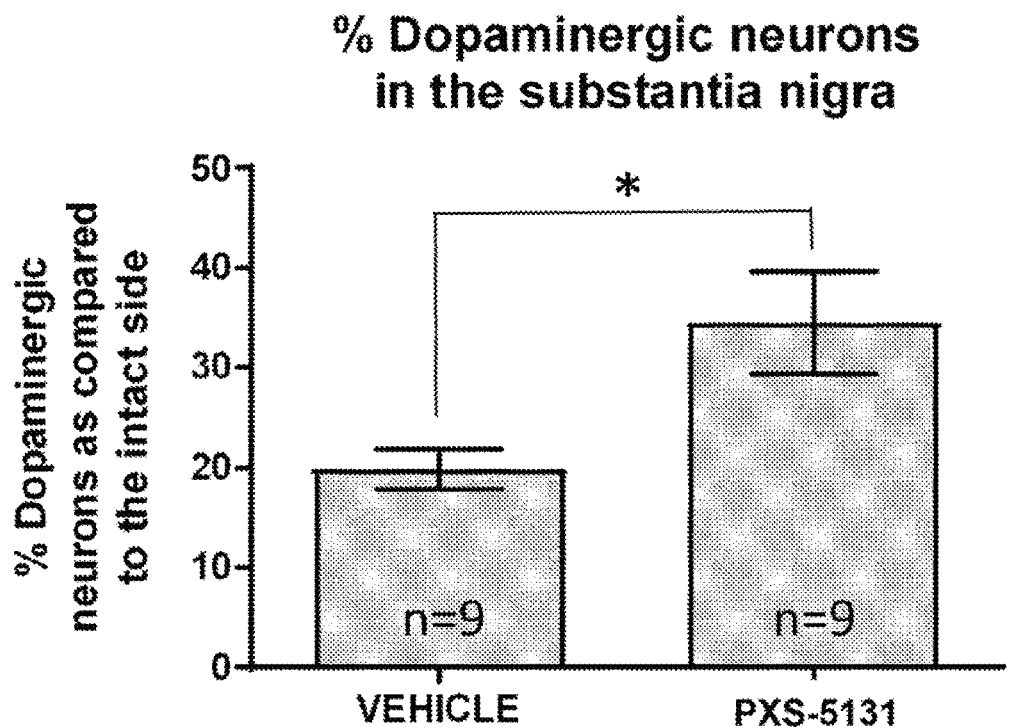
FIG. 5 depicts that PXS-5131 reduces neuronal loss in a Hooded Wistar rat model of dopaminergic neurodegeneration.

As depicted in FIG. 5, unilateral injection of LPS into the substantia nigra of the brain causes a dramatic loss in dopaminergic neurons, when compared to the intact control hemisphere. PXS-5131 administered daily i.p. at 2 mg/kg for 2 weeks afforded significant protection from loss as compared to intact control hemisphere, t-test *$p<0.05$.

Example 17

Efficacy of Dual Inhibitor PXS-5131 in a Mouse Model of Duchenne Muscular Dystrophy mdx mice (C57BL/10ScSn-Dmdmdx/J) were obtained from Jackson Laboratories, Maine, US. Three-months old animals received daily doses of PXS-5131 (6 mg/kg) administered in the chow for thirty days. Untreated, age-matched animals were used as controls. The drug was administered using small palatable gelatin pellets prepared with 10% gelatin in 20% sucralose plus food flavoring (Zhang L. *Protoc. Exch.* 2011, 236) Animals were pre-conditioned to recognize and eat the gelatins with a three-day routine involving overnight fasting followed by exposure of each single animal to the gelatin without the active principle, in the absence of other food. Palatability was further improved by dipping the pellets in corn oil containing trace amounts of almond oil and then breading them with pulverized food pellet.

Muscle function in vivo was assessed for the gastrocnemius muscle, as described by Blaauw B. et al., *Hum. Mol. Genet.* 2008, 17, 3686-3696. Mice were anesthetized, and electrodes were placed on either side of the sciatic nerve, while the common peroneal nerve was cut. Muscle torque production was measured using a lever system (Aurora Scientific 305B). A lever arm of 2.1 mm was used for all groups, as no major differences in body weight between various groups was observed. Eccentric contractions were performed by moving the foot backward at a velocity of 40 mm/s while the gastrocnemius was stimulated with a frequency sufficient to induce full tetanic fusion (100 Hz). Contractions were repeated once every 20 s to avoid inducing fatigue (see FIG. 6).

Figure 6:
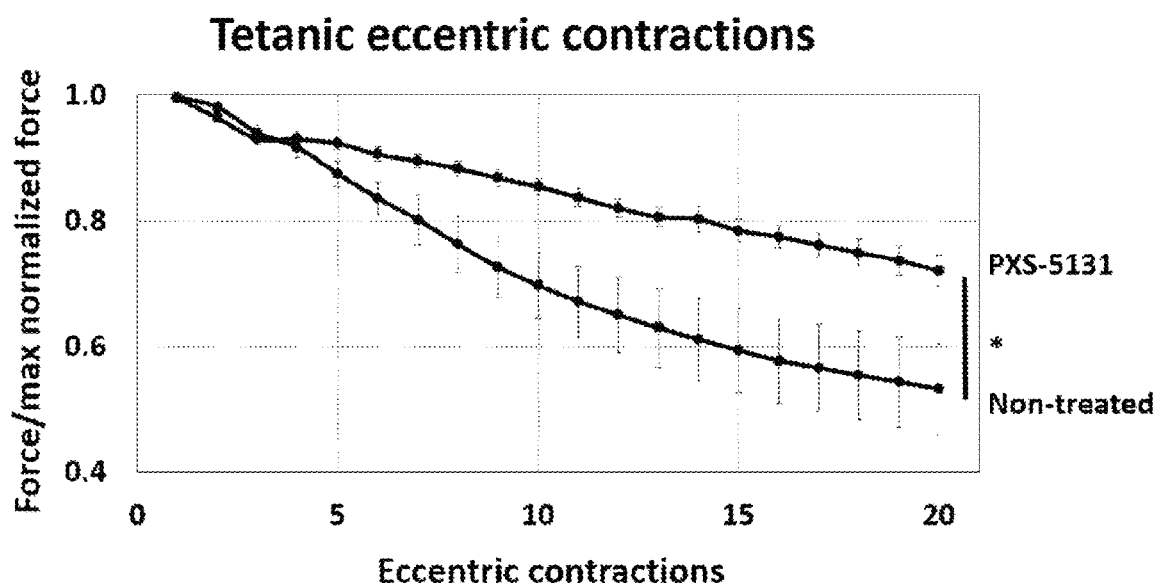
FIG. 6 depicts that oral administration of PXS-5131 at 6 mg/kg/day helps protect against the loss of force caused by eccentric contractions in the gastrocnemius (GC) muscle compared with non-treated age-matched mice after dosing for 4 weeks in 3 months old mdx mice.

FIG. 6 demonstrates that oral administration of PXS-5131 at 6 mg/kg/day helps protect against the loss of force caused by eccentric contractions in the gastrocnemius (GC) muscle compared with non-treated age-matched mice after dosing for 4 weeks in 3 months old mice. *$p<0.05$.

After the force measurements described above, animals were sacrificed by cervical dislocation and the skeletal muscle and the heart (minus the atria) were collected, flash-frozen in isopentane pre-cooled with liquid nitrogen and stored at −80° C. 12 µm sections from a limb muscle (tibialis anterior) were prepared with a cryotome; multiple serial slides were prepared, containing sections from at least three different levels. The same procedure was used to prepare heart transverse sections.

The amount of the neutrophil and macrophage infiltration was determined in serial sections of skeletal muscle prepared as described above, which were fixed and then stained via immunofluorescence with an anti Ly6G and an anti F4/80 antibody (AbCam, ab25377 and ab6640, for neutrophils and macrophages, respectively). The amount of infiltrate was assessed as percentage of fluorophore-positive pixel over the total area of the sections, using Image-J software (FIGS. 7A and B).

The amount of reactive oxygen species (ROS) present in the skeletal muscle tissue sections was assessed using dihydroethidium (DHE, Sigma) as a fluorescent probe in freshly cut tissue sections as described by Menazza et al., et al., *Hum. Mol. Genet.* 2010, 19, 4207-4215. In the presence of ROS, DHE is oxidized forming ethidium, which then can bind to nuclear DNA and emit red fluorescence. The amount of the red fluorescence was then measured from at least 20 random fields per each section using the Metafluor software (Leica), and data were averaged per field (FIG. 7C).

The percentage of fibrotic tissue in skeletal muscle was determined by picrosirius red staining. The sections were treated with xylene for 10 min, 100% ethanol for 2 min, 90% ethanol for 2 min, 70% ethanol for 2 min, distilled water for 2 min and stained with 0.02% Picrosirius red (Sigma, 365548) in saturated aqueous solution of picric acid for 1 min before two fast dips in acetic acid wash (30 mL glacial acetic acid in 200 mL water). Sections were de-hydrated in ascending alcohol concentrations (opposite to that described above) and treated for 10 min in xylene before being mounted with Eukitt (Sigma, cat no. 03989). Whole images of at least three sections per muscle sample were then acquired with a bright field microscope and then analyzed with Image-J software, in order to measure the percentage of fibrotic (red) areas with respect to the total surface (FIG. 7D).

Figure 7:
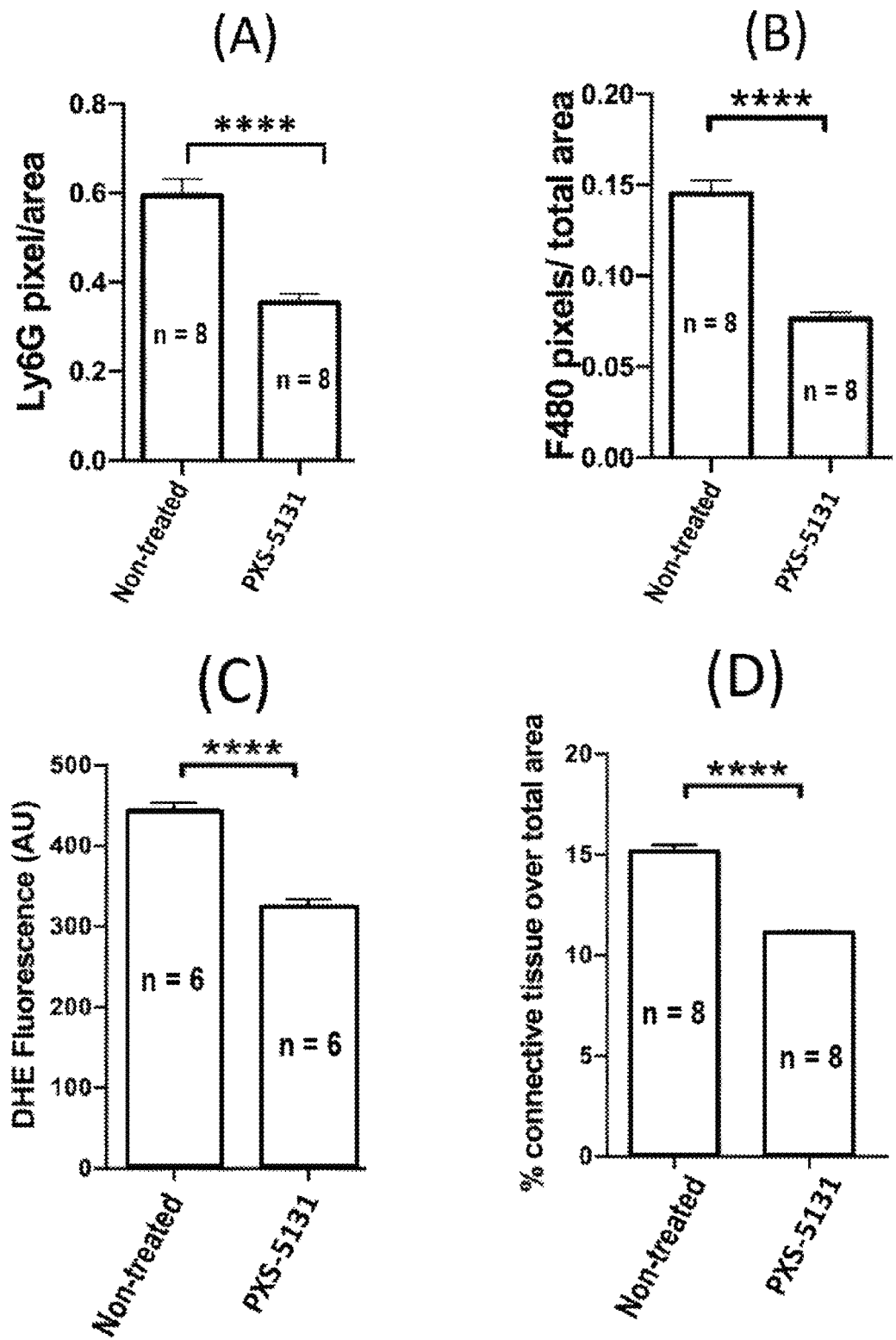
FIG. 7 depicts that oral administration of PXS-5131 at 6 mg/kg/day significantly reduces; (A) neutrophil influx, (B) macrophage influx, (C) reactive oxygen species, and (D) fibrosis (as quantified by picrosirius red staining) in the tibialis anterior muscle, after dosing for 4 weeks in 3 months old mdx mice, compared with non-treated age-matched mice.

As demonstrated in FIG. 7(A-D), oral administration of PXS-5131 at 6 mg/kg/day significantly reduces; (A) neutrophil influx, (B) macrophage influx, (C) reactive oxygen species, and (D) fibrosis (as quantified by picrosirius red staining) in the tibialis anterior muscle, after dosing for 4 weeks in 3 months old mdx mice, compared with non-treated age-matched mice. ****$p<0.0001$ compared to non-treated mice.

Example 18

Method to Determine the Ability of Compounds of Formula I to Inhibit Adipose Tissue SSAO/VAP-1, Muscle and Heart Tissue MAO-B, and Muscle and Heart Tissue MAO-A in Both C57BL/6J Mice and Mdx Mice (C57BL/10ScSn-Dmdmdx/J).

Mice were orally administered the compound under study and sacrificed at various time points and abdominal fat, muscle and heart tissue collected.

SSAO/VAP-1 activity in the adipose tissue was determined as described in EXAMPLE 13.

Skeletal muscle was pulverized in liquid nitrogen and then suspended in ice-cold HEPES buffered media (20 mM HEPES, 0.8% w/v free-fatty acid bovine serum albumin (BSA), 75 mM sucrose, 10 mM EDTA, 215 mM D-mannitol, pH 7.4). Homogenized and then centrifuged at 2,500 rpm for 10 minutes at 4° C. Supernatant transferred and centrifuged at 10,000 rpm for 8 minutes. Supernatant discarded and the resultant pellet containing the mitochondrial extract re-suspended in 0.1 M sodium phosphate buffer solution (1:3 ratio).

Heart muscle was washed with PBS solution three times over ice. Homogenate and extract was then prepared as described for the skeletal muscle.

MAO-B activity was determined by using a specific MAO-A inhibitor (e.g. clorgyline) and an SSAO/VAP-1 inhibitor (e.g. semicarbazide) to establish the high signal. Low signal was established as for the adipose tissue assay (EXAMPLE 13).

MAO-A activity was determined by using a selective MAO-B inhibitor mofegiline (at 30 nM) to establish the high signal and a mixture of specific MAO-A inhibitor (clorgyline) and mofegiline (at 30 nM) to determine the low signal.

Figure 8:
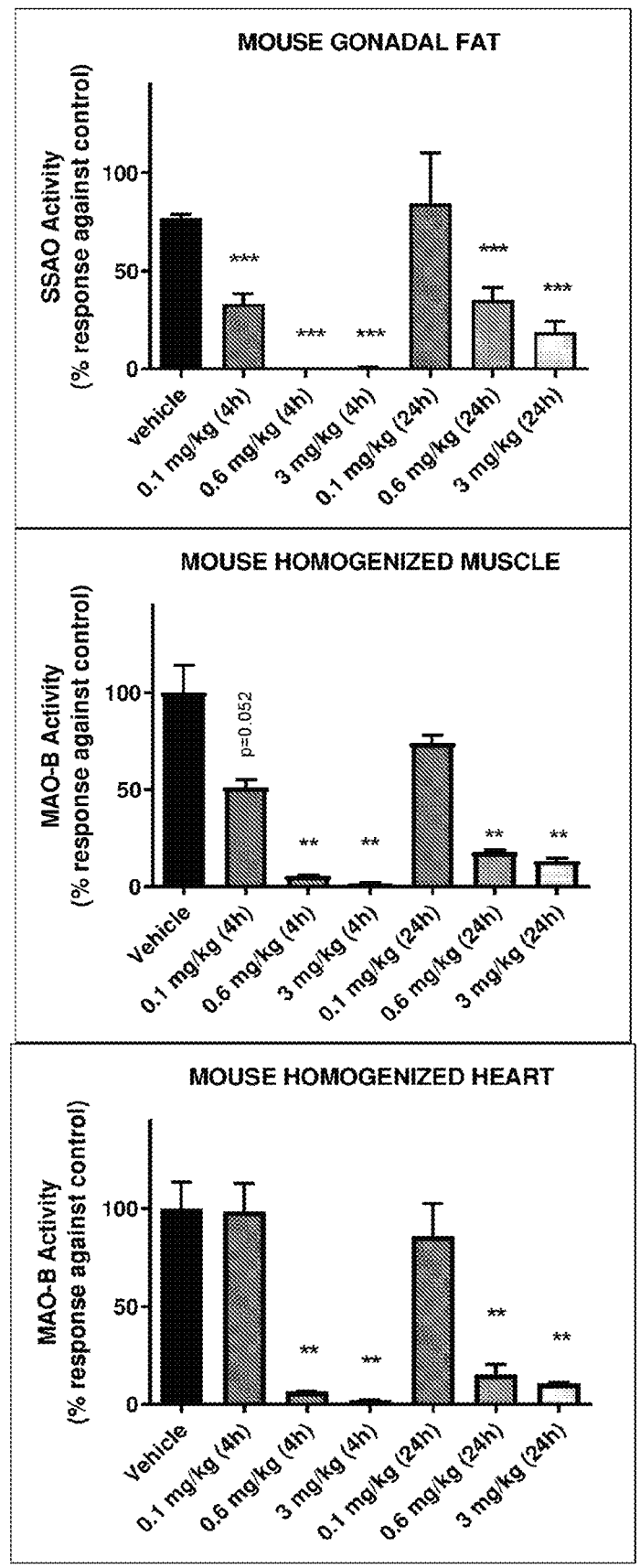
FIG. 8 depicts the MAO-B and SSAO/VAP-1 inhibition in C57BL/6J mouse, heart, muscle and adipose tissue, after oral administration of Compound 1 at various doses.
Figure 9:
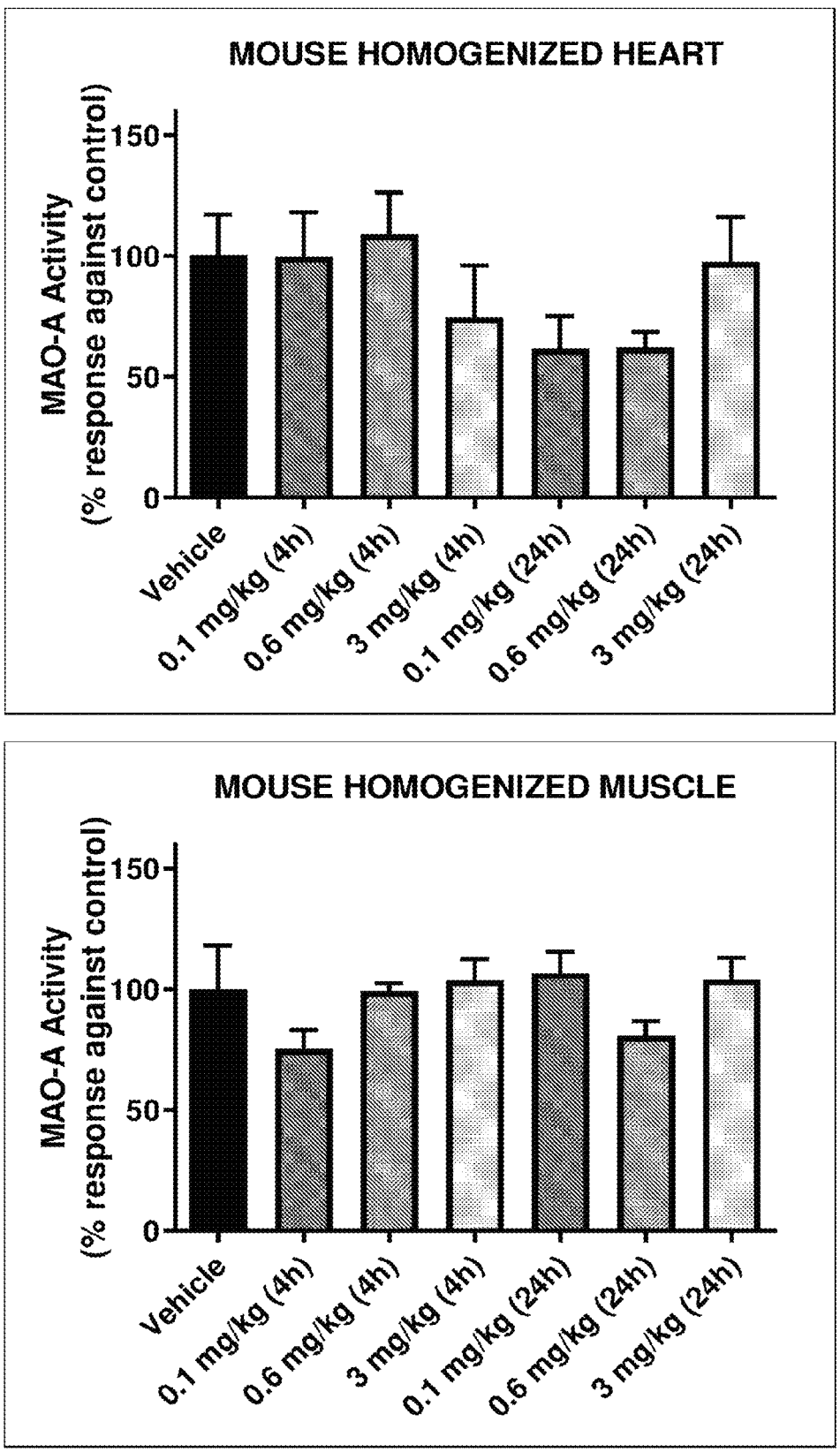
FIG. 9 depicts the activity of MAO-A from C57BL/6J mouse heart and muscle tissue, after oral administration of Compound 1 at various doses.

Activity of the treated samples was analyzed using the fluorometric method described in EXAMPLE 9 for SSAO/VAP-1 activity, EXAMPLE 10 for MAO-B and EXAMPLE 11 for MAO-A activity (FIG. 8 and FIG. 9).

As depicted in FIG. 8, a single dose of Compound 1 affords a dose-related reduction in both SSAO/VAP-1 and MAO-B activity at 4 hours after administration in C57BL/6J mice. At the 24-hour time point inhibition of the enzyme activity is still evident. $*p<0.05$, $p<0.01$ and $*p<0.001$ compared to vehicle treated mice.

As depicted in FIG. 9, a single dose of Compound 1 has no inhibitory effect on the heart and muscle MAO-A activity 4 and 24 hours after administration in C57BL/6J mice.

A similar profile of inhibition was observed when Compound 1 was administered to mdx mice (C57BL/10ScSn-Dmdmdx/J) at a dose of 4.8 mg/kg/day over 3 days.

Figure 10:
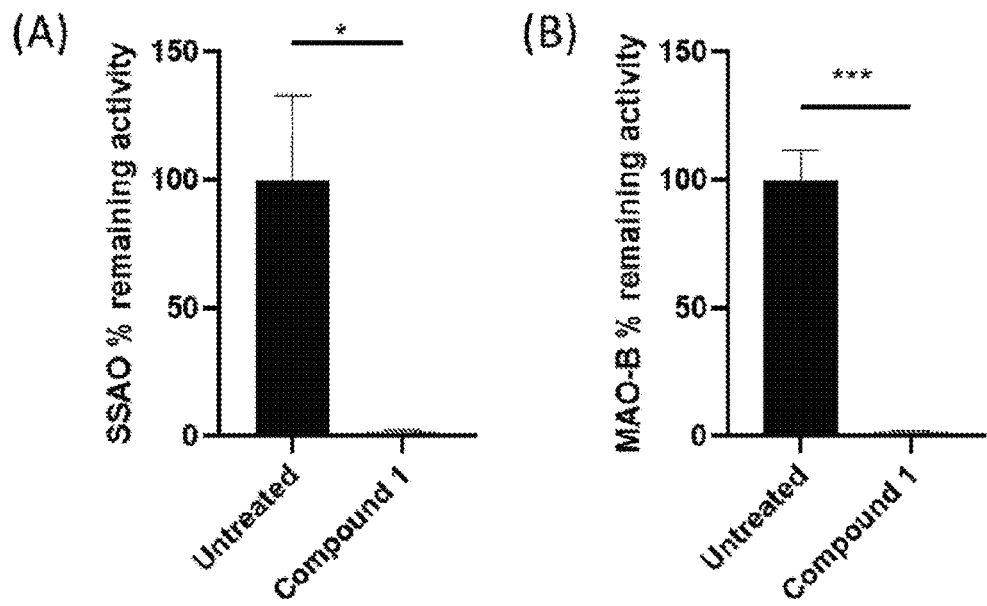
FIG. 10 depicts the MAO-B and SSAO/VAP-1 inhibition in mdx mouse, muscle and adipose tissue, respectively, after oral administration of Compound 1.

As depicted in FIG. 10, a single dose of Compound 1 completely inhibits adipose tissue SSAO/VAP-1 and muscle MAO-B activity in C57BL/10ScSn-Dmdmdx/J mice. $*p<0.05$, and $***p<0.001$ compared to vehicle treated mice.

Figure 11:
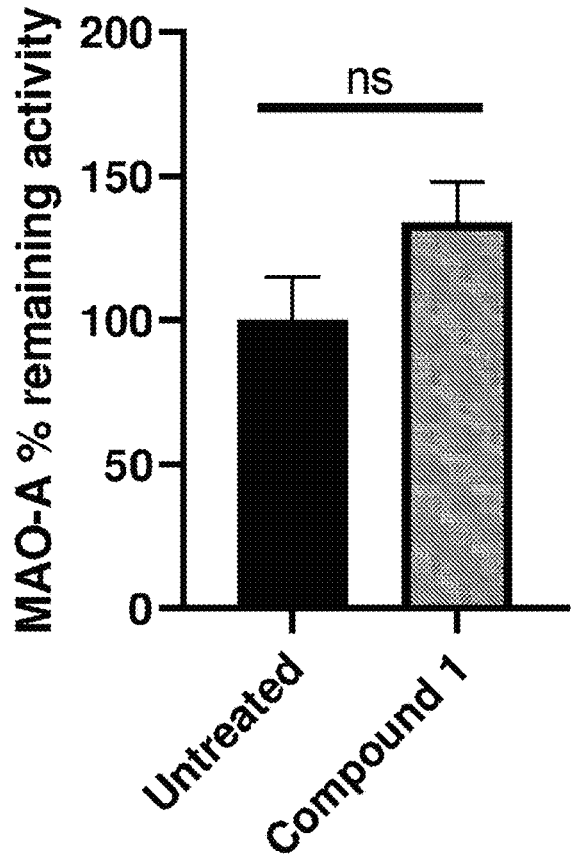
FIG. 11 depicts the activity of MAO-A from mdx mouse muscle tissue, after oral administration of Compound 1.

As depicted in FIG. 11, a single dose of Compound 1 has no inhibitory effect on the muscle MAO-A after administration in C57BL/10ScSn-Dmdmdx/J mice.

Example 19

Efficacy of Dual Inhibitor Compound 1 in a Mouse Model of Duchenne Muscular Dystrophy Three-months old mdx mice (C57BL/10ScSn-Dmdmdx/J) received daily doses of Compound 1 (in a range of 1-6 mg/kg) administered in the drinking water for thirty days. Untreated, age-matched animals were used as controls. A second cohort of mice aged 10 months-old received daily doses of Compound 1 (in a range of 1-6 mg/kg) administered in the drinking water for ninety days. Untreated, age-matched animals were used as controls.

After the end of each treatment period, animals were sacrificed by cervical dislocation and the skeletal muscle and the heart (minus the atria) collected, flash-frozen in isopentane pre-cooled with liquid nitrogen and stored at −80° C. 12 µm sections from the diaphragm muscle were prepared with a cryotome; multiple serial slides were prepared, containing sections from at least three different levels. The same procedure was used to prepare heart transverse sections.

The amount of the neutrophil and macrophage infiltration, reactive oxygen species (ROS) present and the percentage of fibrotic tissue, was determined as described in EXAMPLE 17.

Figure 12:
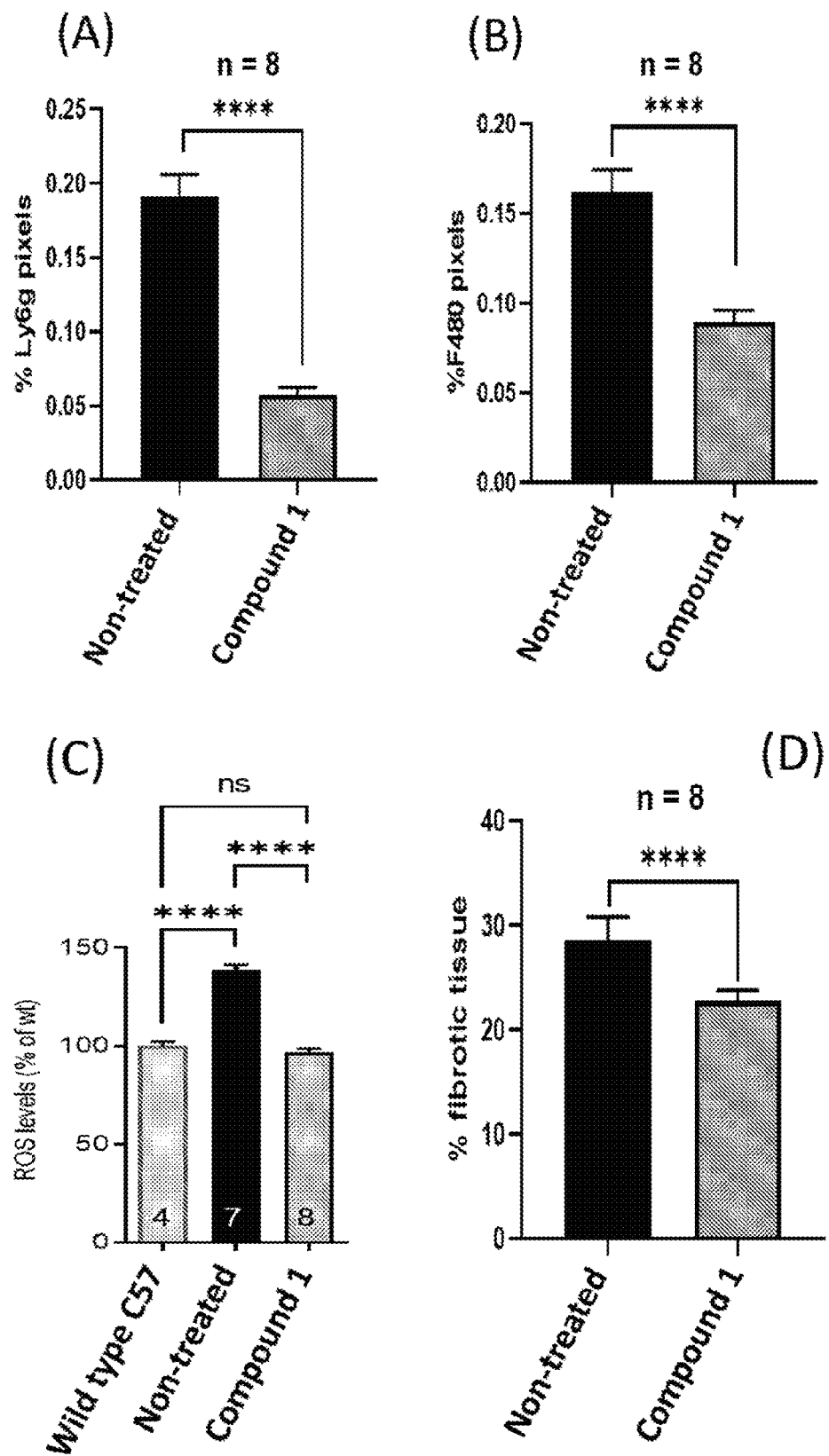
FIG. 12 depicts that oral administration of Compound 1 (4.8 mg/kg/day) significantly reduces; (A) neutrophil influx, (B) macrophage influx, (C) reactive oxygen species, and (D) fibrosis (as quantified by picrosirius red staining) in the diaphragm muscle, after dosing for 30 days in 3 months-old mdx mice, compared with non-treated age-matched mice.

As demonstrated in FIG. 12(A-D), oral administration of Compound 1 at 4.8 mg/kg/day significantly reduces; (A) neutrophil influx, (B) macrophage influx, (C) reactive oxygen species, and (D) fibrosis (as quantified by picrosirius red staining) in the diaphragm muscle, after dosing for thirty days in 3 months-old mdx mice, compared with non-treated age-matched mice. $****p<0.0001$ compared to non-treated mice.

Figure 13:
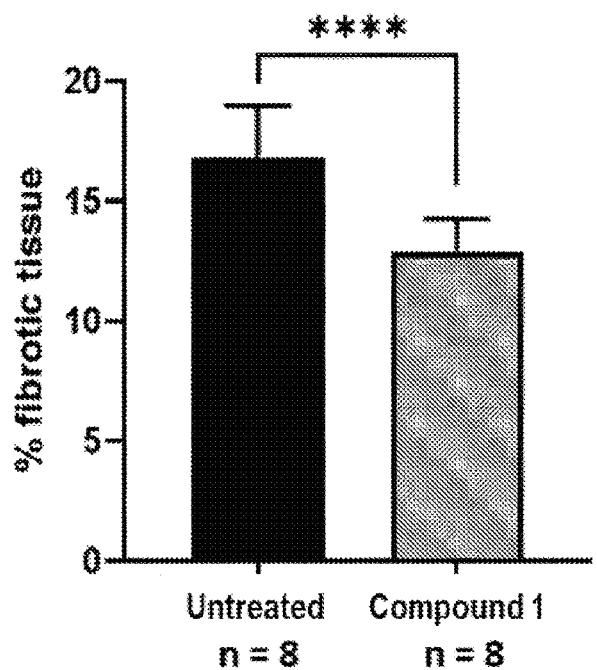
FIG. 13 depicts that oral administration of Compound 1 (4.8 mg/kg/day) significantly reduces cardiac fibrosis (as quantified by picrosirius red staining of heart muscle), after dosing for 90 days in 10 months-old mdx mice, compared with non-treated age-matched mice.

As demonstrated in FIG. 13, oral administration of Compound 1 at 4.8 mg/kg/day significantly reduces cardiac fibrosis (as quantified by picrosirius red staining in the heart muscle), after dosing for ninety days in 10 months-old mdx mice, compared with non-treated age-matched mice. $****p<0.0001$ compared to non-treated mice.

Example 20

Assessment of the metabolic stability profile of Compound 1 using standardized commercially available methods (available through contract research organizations such as Eurofins Panlabs Inc, (https://www.eurofinsdiscoveryservices.com/services/in-vitro-assays/) or Evotec SE, (https://www.evotec.com/en/execute/integrated-pre-clinical-development/adme)).

The potential for metabolism in vivo was evaluated in vitro using the following assays:

Liver microsomal stability (human, rat, dog; in presence of NADPH)

Hepatocyte stability (human, rat, dog)

Plasma stability (human, rat, dog)

Whole blood stability (human, rat)

Simulated gastric fluid stability (10 µM test article, pH 1.2)

Metabolite identification in human hepatocytes

Compound 1 was found to have favourable metabolic stability in all assays.

Example 21

Assessment of the off-target profile of Compound 1 using standardized commercially available methods (available through contract research organizations such as Eurofins Panlabs Inc, (https://www.eurofinsdiscoveryservices.com/services/in-vitro-assays/) or Evotec SE, (https://www.evotec.com/en/execute/integrated-pre-clinical-development/adme)).

The potential for off-target promiscuity in vivo was evaluated in vitro using the following assays:

Inhibition of cytochrome P450 activity (30 µM single concentration; 1A2, 2B6, 2C8, 2C9, 2C19, 2D6, 3A4)

Eurofins Discovery Safety Screen panel of 44 enzymes, receptors, ion channels and transporters (percentage inhibition at 10 µMconcentration).

Eurofins Transporter Protein Screen panel of 13 common transporters (percentage inhibition at 10 µM concentration).

Aptuit Cardiac Ion Channel panel of 7 targets (automated patch clamp assay; concentration 0 up to 300 µM).

Compound 1 was found to have a favorable off-target profile in all assays.

Example 22

Assessment of the Cytotoxicity Profile of Compound 1 in a Miniaturized Bacterial Reverse Mutagenicity Screening Assay.

Compound 1 was tested for mutagenic potential in a miniaturized reverse mutation assay using Salmonella typhimurium strains TA98, TA100 and Escherichia. coli WP2 uvrA pKM101 in the presence and absence of a metabolic activation system. The test article was formulated in dimethylsulfoxide (DMSO) at nominal concentration of 50 mg/mL and serial dilutions were made from this stock solution. Final dosing concentrations were 1000, 500, 250, 125, 62.5, 31.3, 15.6 and 7.81 µg/well for the test article. Metabolic activation was provided using an S9 mix containing 10% v/v Aroclor-1254-induced rat liver S9 (Regensys System reagents, Moltox, Boone, NC).

Compound 1 did not induce a response indicative of mutagenic potential in this assay.

Example 23

Assessment of the Potential of Compound 1 to Induce Phospholipidosis in a Cell-Based Fluorescence Assay.

Compound 1 was tested in vitro for the potential to induce phospholipidosis according to the method outlined by Fujimura et. al. (*Experimental and Toxicologic Pathology*, 2007, 58, 375-382) at concentrations up to 100 μM.

Compound 1 had no effect on the cellular phenotype nor cell viability in this assay.

Example 24

Stability of Compound 1 in a Grape Syrup Formulation at Room Temperature

Methylparahydroxybenzoate (126.2 mg), propylparahydroxybenzoate (20.0 mg), sodium phosphate monobasic (1%, 1.0 g) and saccharose (16.56 g) were dissolved in 100 mL purified water, vortexed for 10 min, followed by sonication for 30 min, and then filtered through a 0.45 μm filter. pH adjusted to pH 5 using 0.5 M NaOH. To 50 mL of the resultant solution was added grape flavor (LorAnnOils, 0180-0800; 1%, 0.5 mL), followed by 50 mg of Compound 1 to attain a final concentration of 1 mg/mL. Split into two 25 mL portions, one frozen, and one left at room temperature (rt) in a sealed falcon tube.

As shown in TABLE 4, after 91 days at room temperature, no discernible degradation of Compound 1 was observed.

TABLE 4

| Purity of Compound 1 stored at −20° C. for 91 days as measured by HPLC/area under the curve at 265 nm | Purity of Compound 1 stored at rt for 91 days as measured by HPLC/area under the curve at 265 nm |
| --- | --- |
| 99.781% | 99.785% |

The invention claimed is:

1. A compound of Formula I:

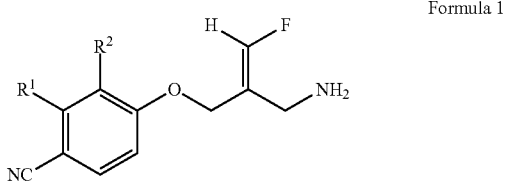

Formula 1 or a pharmaceutically acceptable salt, polymorphic form or solvate thereof; wherein:
$R^1$ is selected from the group consisting of hydrogen, fluorine, bromine and methyl; and
$R^2$ is hydrogen or fluorine.

2. The compound according to claim 1 selected from the group consisting of:

| Compound no. | Structure | Chemical name |
| --- | --- | --- |
| 1 | 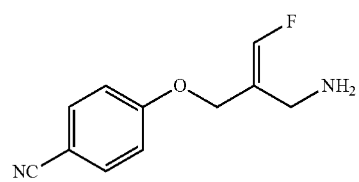 [SMILES: N#Cc1ccc(OC/C(=C/F)CN)cc1] | (E)-4-((2-(aminomethyl)-3-fluoroallyl)oxy)benzonitrile |
| 2 | 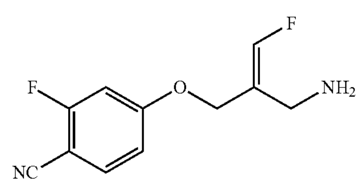 [SMILES: N#Cc1ccc(OC/C(=C/F)CN)cc1F] | (E)-4-((2-(aminomethyl)-3-fluoroallyl)oxy)-2-fluorobenzonitrile |
| 3 | 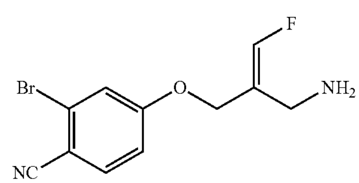 [SMILES: N#Cc1ccc(OC/C(=C/F)CN)cc1Br] | (E)-4-((2-(aminomethyl)-3-fluoroallyl)oxy)-2-bromobenzonitrile |
| 4 | 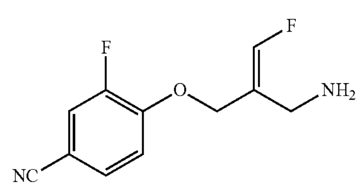 [SMILES: N#Cc1ccc(OC/C(=C/F)CN)c(F)c1] | (E)-4-((2-(aminomethyl)-3-fluoroallyl)oxy)-3-fluorobenzonitrile |

| Compound no. | Structure | Chemical name |
|---|---|---|
| 5 | Me, O, NH₂, F, NC | (E)-4-((2-(aminomethyl)-3-fluoroallyl)oxy)-2-methylbenzonitrile | or a pharmaceutically acceptable salt or solvate thereof.

3. A pharmaceutical composition comprising a compound according to claim 1 or 2, or a pharmaceutically acceptable salt or solvate thereof, and at least one pharmaceutically acceptable excipient, carrier or diluent.

4. A method of inhibiting the amine oxidase activity of semicarbazide-sensitive amine oxidase/vascular adhesion protein-1 (SSAO/VAP-1) and monoamine oxidase B (MAO-B) in a subject in need thereof, comprising administering to the subject an effective amount of a compound according to claim 1 or 2, or a pharmaceutically acceptable salt or solvate thereof.

5. A method of treating or preventing a disease or disorder by inhibiting the activity of the SSAO/VAP-1 protein and the MAO-B protein, comprising administering to a subject in need thereof a therapeutically effective amount of a compound according to claim 1 or 2, or a pharmaceutically acceptable salt or solvate thereof.

6. The method according to claim 5, wherein the disease or disorder is ameliorated by the selective inhibition of SSAO/VAP-1 and MAO-B relative to MAO-A.

7. The method according to claim 5, wherein the disease is a neuromuscular disorder.

8. The method according to claim 7, wherein the neuromuscular disorder is muscular dystrophy.

9. The method according to claim 8, wherein the muscular dystrophy is selected from the group consisting of Duchenne muscular dystrophy (DMD), Becker muscular dystrophy, facioscapulohumeral muscular dystrophy and myotonic dystrophy.

10. The method according to claim 5, wherein the disease is a neurodegenerative or a neuroinflammatory disease.

11. The method according to claim 10, wherein the neurodegenerative or the neuroinflammatory disease is selected from the group consisting of Alzheimer's disease, Parkinson's disease, multiple sclerosis, Huntington's disease, amyotrophic lateral sclerosis, spinal muscular atrophy, myasthenia gravis and Charcot-Marie-Tooth disease.

\* \* \* \* \*